United States Patent
Deng et al.

(10) Patent No.: US 9,981,025 B2
(45) Date of Patent: *May 29, 2018

(54) ANTI-DRUG VACCINES

(71) Applicant: THE TRUSTEES OF COLUMBIA UNIVERSITY IN THE CITY OF NEW YORK, New York, NY (US)

(72) Inventors: Shi-Xian Deng, White Plains, NY (US); Donald W. Landry, New York, NY (US); Gavreel Kalantarov, Fort Lee, NJ (US); Ilya Trakht, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/827,191

(22) Filed: Aug. 14, 2015

(65) Prior Publication Data

US 2015/0343042 A1 Dec. 3, 2015

Related U.S. Application Data

(60) Division of application No. 13/452,019, filed on Apr. 20, 2012, now Pat. No. 9,173,874, which is a continuation of application No. PCT/US2010/053539, filed on Oct. 21, 2010.

(60) Provisional application No. 62/254,060, filed on Oct. 22, 2009.

(51) Int. Cl.
| | |
|---|---|
| A61K 39/13 | (2006.01) |
| A61K 31/44 | (2006.01) |
| A61K 39/395 | (2006.01) |
| A61K 47/48 | (2006.01) |
| A61K 39/00 | (2006.01) |
| A61K 39/385 | (2006.01) |
| A61K 47/64 | (2017.01) |

(52) U.S. Cl.
CPC .......... *A61K 39/0013* (2013.01); *A61K 31/44* (2013.01); *A61K 39/385* (2013.01); *A61K 47/643* (2017.08); *A61K 47/646* (2017.08); *A61K 2039/505* (2013.01); *A61K 2039/55566* (2013.01); *A61K 2039/6056* (2013.01); *A61K 2039/6081* (2013.01)

(58) Field of Classification Search
CPC .. A61K 31/44; A61K 39/0013; A61K 39/385; A61K 47/643; A61K 47/646; A61K 2039/6056; A61K 2039/505; A61K 2039/55566; A61K 2039/6081
See application file for complete search history.

(56) References Cited

U.S. PATENT DOCUMENTS

| | | | |
|---|---|---|---|
| 4,102,979 A | 7/1978 | Christenson | |
| 6,184,013 B1* | 2/2001 | Landry | A61K 47/48384 435/188.5 |
| 6,383,490 B1 | 5/2002 | Wirsching et al. | |
| 6,437,092 B1 | 8/2002 | Ezrin et al. | |
| 6,579,696 B1* | 6/2003 | Shekhani | G01N 33/532 435/68.1 |
| 6,663,861 B2 | 12/2003 | Hansen et al. | |
| 6,699,474 B1 | 3/2004 | Cerny et al. | |
| 6,932,971 B2 | 8/2005 | Bachmann et al. | |

FOREIGN PATENT DOCUMENTS

WO WO2009/120954 * 10/2009

OTHER PUBLICATIONS

Chen et al., Nanjing Nongye Daxue Xuebao, 21(3), 84-88, (Chinese) 1998, English abstract only.*
Strop et al., Chemistry Biology 20: 161-167, Feb. 21, 2013.*
Kinsey et al., Expert Rev Vaccines 9(9): 1109-1114, Sep. 2010.*
U.S. Appl. No. 13,452,019 (U.S. Pat. No. 9,173,874), filed Apr. 20, 2012 (Nov. 3, 2015).
U.S. Appl. No. 13/452,019, dated Jun. 20, 2013 Non-Final Office Action.
U.S. Appl. No. 13/452,019, dated Oct. 21, 2013 Response to Non-Final Office Action.
U.S. Appl. No. 13/452,019, dated Jan. 3, 2014 Final Office Action.
U.S. Appl. No. 13/452,019, dated Jul. 3, 2014 Amendment and Request for Continued Examination (RCE).
U.S. Appl. No. 13/452,019, dated Nov. 5, 2014 Non-final Office Action.
U.S. Appl. No. 13/452,019, dated May 5, 2015 Response to Non-Final Office Action.
U.S. Appl. No. 13/452,019, dated Jun. 22, 2015 Notice of Allowance.
U.S. Appl. No. 13/452,019, dated Sep. 17, 2015 Issue Fee Payment.
"Celtic Pharma Reports Preliminary Results of Phase 2 Clinical Trials with TA-CD, Cocaine Addiction Vaccine", Celtic Pharma, Press Release http://www.celticpharma.com/news/pr/release-062106.pdf (2006) ☐.
Bagasra, et al., A potential vaccine for cocaine abuse prophylaxis:, Immunopharmacology, 23:173-179 (1992).
Deng, et al., "Covalent modification of proteins by cocaine", PNAS, 99(6):3412-3416 (Mar. 19, 2002).
Ettinger, et al., "Active immunization with cocaine-protein conjugate attenuates cocaine effects", Pharmacol. Biochem Behav., 58(1):215-220 (1997).
Gallacher, "A potential vaccine for cocaine abuse prophylaxis?", Immunopharmacology, 27(1):79-81 (1994).
Gao, et al., "The concept of pharmacologic cocaine interception as a treatment for drug abuse", Chemico-Biological Interactions, 187:421-424 (2010).
Hall, et al., "Ethical issues in using a cocaine vaccine to treat and prevent cocaine abuse and dependence", J. Med. Ethics, 30(4):337-340 (2004).

(Continued)

*Primary Examiner* — Phuong Huynh
(74) *Attorney, Agent, or Firm* — Baker Botts L.L.P.

(57) ABSTRACT

The present invention relates to anti-drug vaccines based on conjugates between the drug and a non-immunogenic carrier protein. In preferred embodiments, it provides for anti-cocaine vaccines and their use to diminish the effects and/or use of cocaine in a subject.

7 Claims, 21 Drawing Sheets

(56) References Cited

OTHER PUBLICATIONS

Figure 3A:
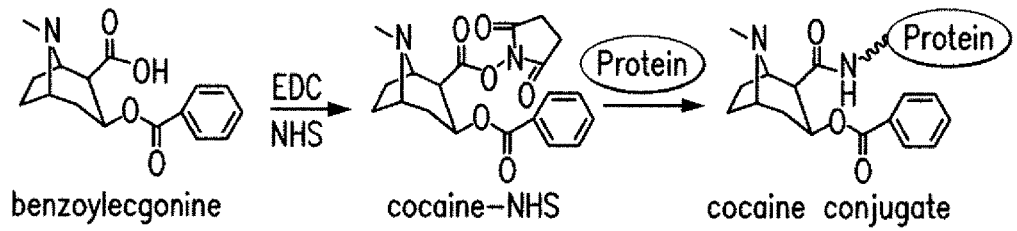

Haney, et al., "Therapeutic vaccines for substance dependence", Expert Rev. Vaccines, 3(1):11-18 (2004).

Hrafnkelsdottir, et al., "Induction of protective and specific antibodies against cocaine by intranasal immunisation using a glyceride adjuvant", Biol., Pharm. Bull., 28(6):1038-1042 (2005).

International Search Report and Written Opinion for PCT/US2010/053539, dated Dec. 21, 2010 (Corresponds to U.S. Appl. No. 13/452,019).

Kalantarov, et al., "A stroll human anti-cocaine antibody realm", Intradepartmental Seminar at Columbia University, May 29, 2009 (whole document).

Kantak, et al., "Evaluation of anti-cocaine antibodies and a cocaine vaccine in a rat self-administration model", Psychopharmacology, 148(3):251-262 (2000).

Kinsey, et al., "Anti-cocaine vaccine development", Expert Reviews Vaccines, 9(9):1109-1114 (2010).

Kinsey, et al., "Anti-drug vaccines to treat substance abuse", Immunol Cell Biol., 87(4):309-314 (2009).

Kinsey, et al., Active immunotherapy for the treatment of cocaine dependence, Drugs Future, 35(4):301-306 (2010).

Kosten, et al., "Human therapeutic cocaine vaccine: safety and immunogenicity", Vaccine, 20(7-8):1196-204 (2002).

Kosten, et al., "Immunotherapy for the treatment of drug abuse", Pharmacol. Ther., 108(1):76-85 (2005).

Kosten, et al., "Vaccines for Addiction", Presentation slides, http://www.apa.org/about/gr/science/advocacy/2008/Kosten_presentation.pdf, (2008).

Martell, et al., "Vaccine pharmacotherapy for the treatment of cocaine dependence", Biol Psychiatry, 58(2):158-164 (2005).

Montoya, "Inmuoterapias para las adicciones a las drogas [Immunotherapies for drug addictions]", Addiciones, 20(2):111-115 (2008).

Moreno, et al., "Immunopharmacotherapy: Vaccination strategies as a treatment for drug abuse and dependence", Pharmacology, Biochemistry and Behavior, 92(2):199-205 (2009).

Morris, "Hope and caution over cocaine vaccine has never been higher", The Lancet, 3:451 (2004).

Orson, et al., "Substance abuse vaccines", Ann. NY Acad. Sci., 1141:257-269 (2008).

Orson, et al., "Vaccines for cocaine abuse: Experimental and clinical evidence for efficacy", AAPS National Biotechnology Conference, Jun. 21-24, 2009, Seattle, WA (program and slides).

Orson, et al., "Vaccines for cocaine abuse", Human Vaccines, 5(4):194-199 (2009).

Shearer, et al., Feasibility, rationale and prospects for therapeutic cocaine vaccines, NDARC Technical Report No. 168, National Drug and Alcohol Research Centre, pp. 3-26 (2003).

Sofuoglu, et al., "Emerging pharmacological strategies in the fight against cocaine addiction", Expert Opin Emerg Drugs, 11(1):91-98 (2006).

Zhu, et al., "Complete reaction cycle of a cocaine catalytic antibody at atomic resolution", Structure, 14(2):205-216 (2006).

\* cited by examiner

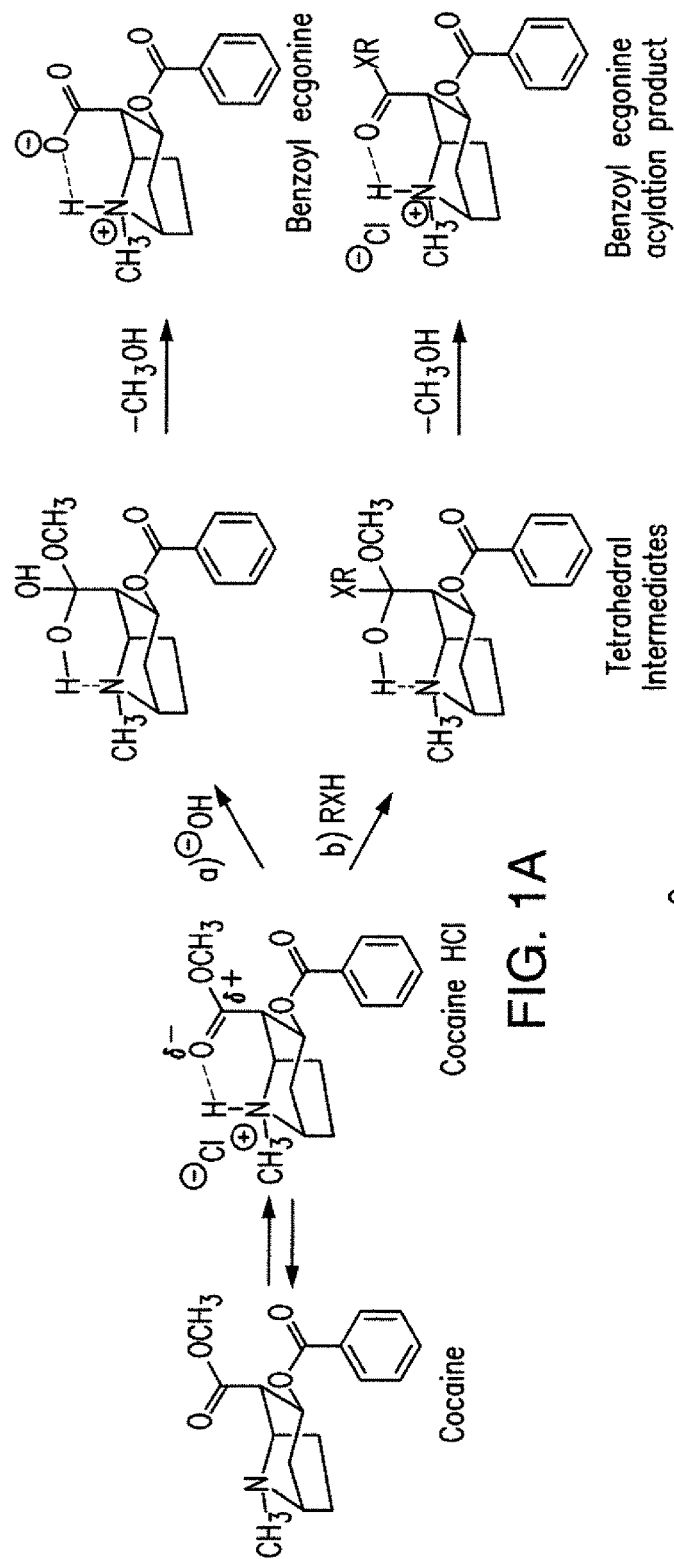
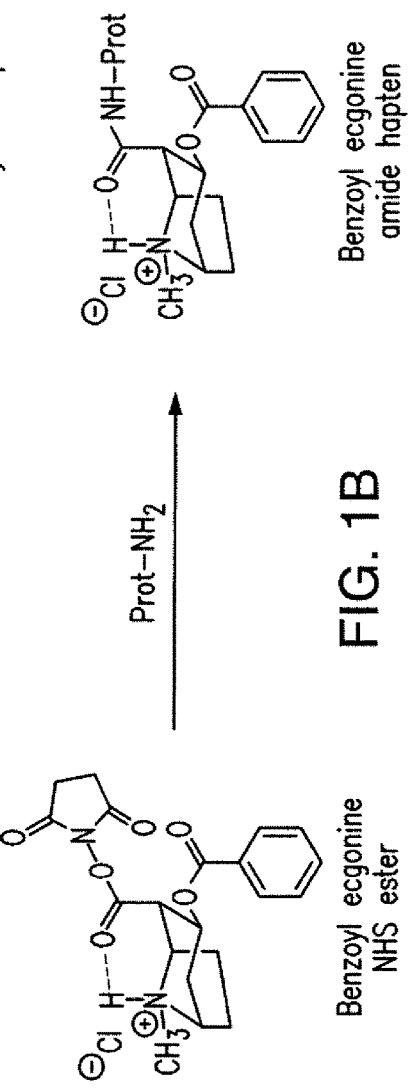
FIG. 1A
FIG. 1B

Chemical Configuration of Several Immunogens

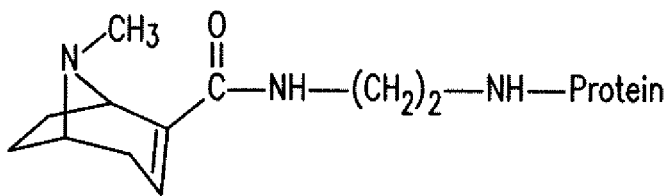

The structure of Ecgonidine (ECD) with EDA linker protein conjugates

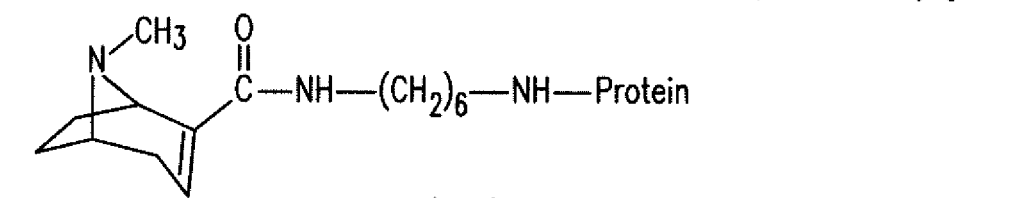

The structure of Ecgonidine (ECD) with HDA linker protein conjugates

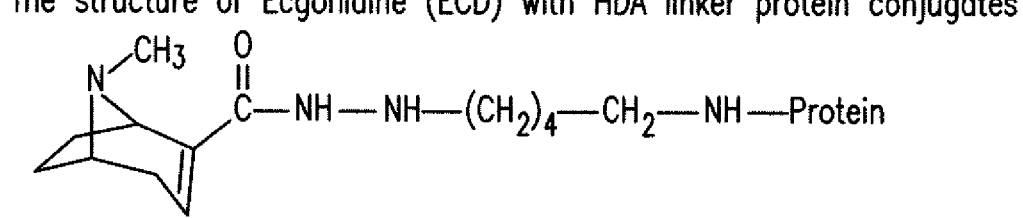

The structure of AEME with Glutaraldehyde linker protein conjugates

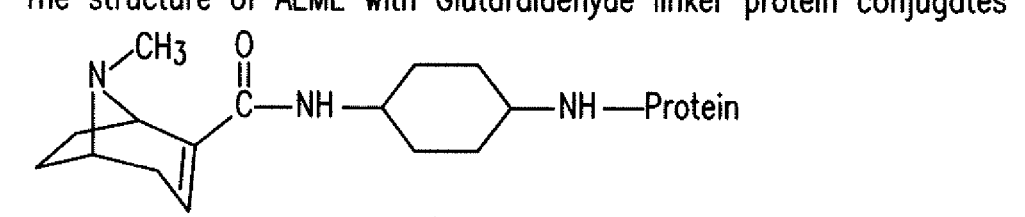

The structure of Ecgonidine (ECD) with CDA linker protein conjugates

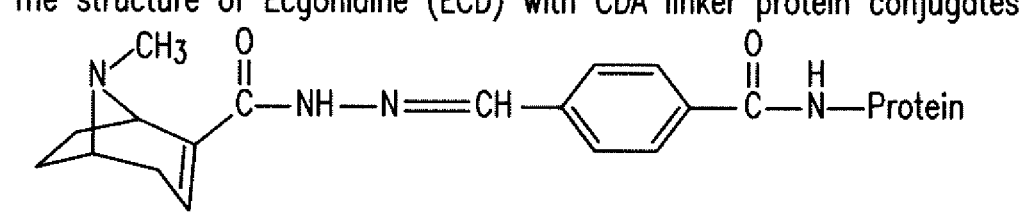

The structure of AEME with CBA linker protein conjugates

FIG. 2

Synthesis of Cocaine Conjugates

Synthesis of Cocaine Conjugates

Synthesis of Cocaine Conjugates

B-lymphocytes donors:

- Hepatitis C - chronic or acute stage
- History of drug abuse (cocaine, heroin, marijuana)
- Hep B, HIV, TB

| Fusion ID | age/race | death | history | wells grown (96-well plates) | wells positive | isotype |
|---|---|---|---|---|---|---|
| VCR364 | 44CF | head trauma | cocaine-18 months | 386 | 1 (1D7) | IgM, kappa |
| VL0456 | 35CF | head trauma | cocaine-1999-04, marijuana | 386 | 1(1D8D6) | IgM, kappa |
| WBJ067 | 29HF | anoxia | heroin, short cocaine | 288 | 1(F2D4) | Igm, lambda |
| WCF183 | 38HM | ICH | marijuana | 288 | 1(C3) | IgM, ? |

FIG. 4

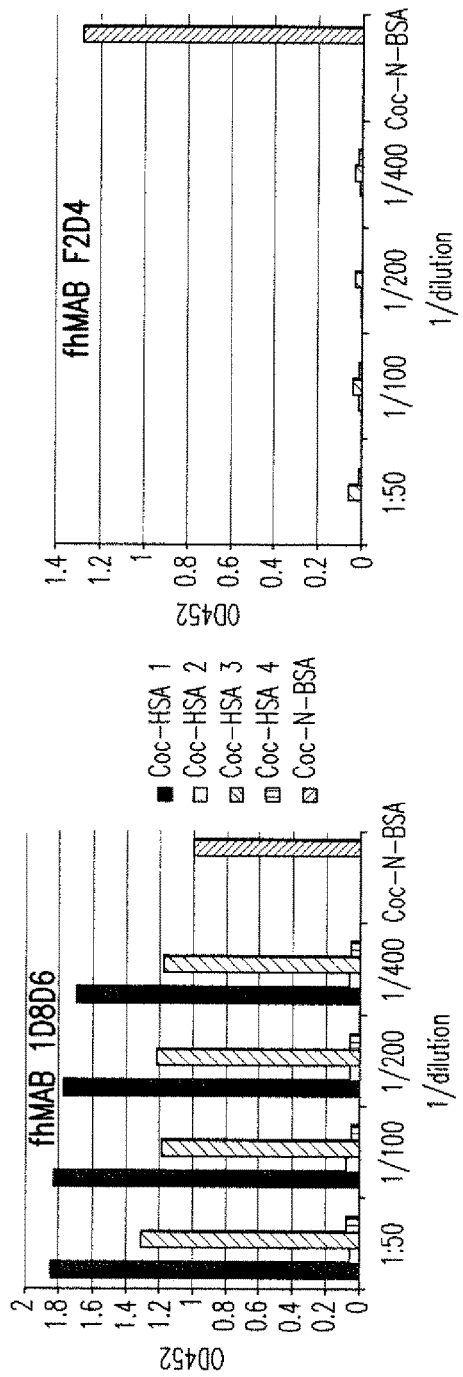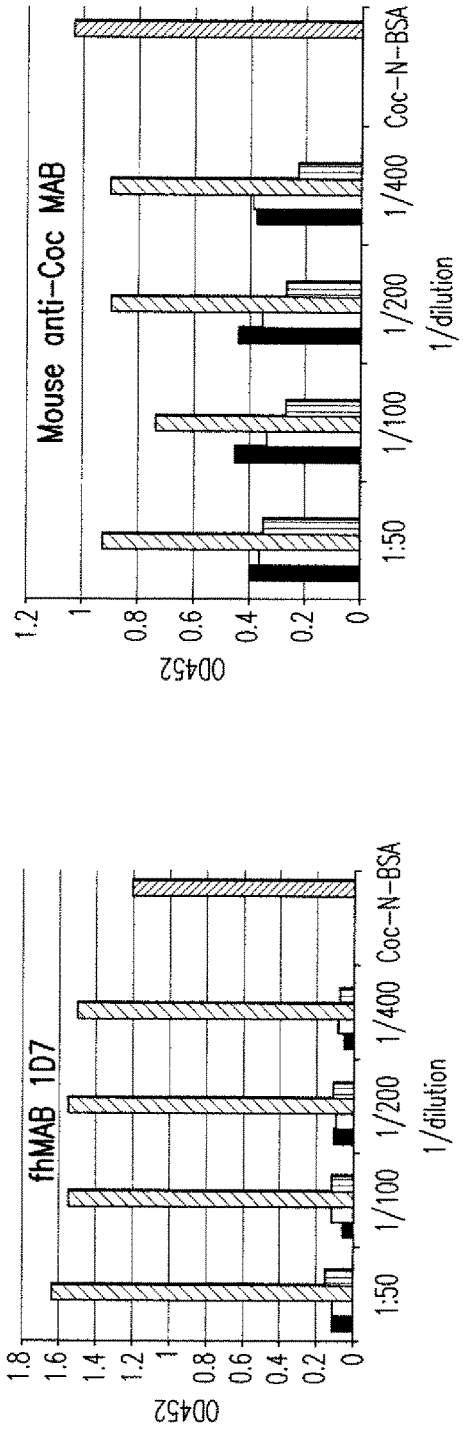

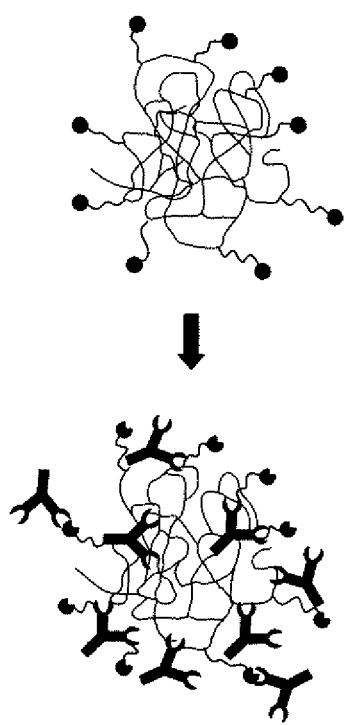 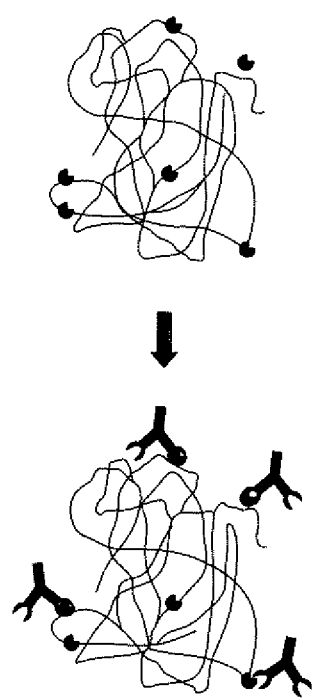
FIG. 18A                    FIG. 18B

ANTI-DRUG VACCINES

PRIORITY CLAIM

This Application is a divisional application of U.S. patent application Ser. No. 13/452,019 filed on Apr. 20, 2012, which granted as U.S. Pat. No. 9,173,874 on Nov. 3, 2015 which is a continuation of International Patent Application Serial No. PCT/US10/053539 filed Oct. 21, 2010, which claims priority to U.S. Provisional Application Ser. No. 61/254,060 filed Oct. 22, 2009, priority to each of which is claimed, and the contents of each of which are hereby incorporated by reference in their entireties herein.

GRANT INFORMATION

Government funds were not used to develop the subject matter of this invention.

1. INTRODUCTION

The present invention relates to anti-drug vaccines based on conjugates between the drug and a non-immunogenic "Self" carrier protein. While described primarily with regard to anti-cocaine vaccines, the invention may be applied to other drugs, such as nicotine, heroin etc.

2. BACKGROUND OF THE INVENTION

Cocaine addiction is a serious public health issue that impacts the physical and emotional well-being and productivity of our society. It is a worldwide problem—Sofuoglu and Kosten (2006, Expert Opin. Emerging Drugs 11(1):91-98) estimate that there are 14 million cocaine users worldwide, two-thirds of which reside in the Americas (citing the 2005 World Drug Report published on line by the United Nations, Office on Drugs and Crimes). It has been estimated that as many as one in six individuals who use cocaine will become dependent on it (Hall and Carter, 2004, J. Med. Ethics 30:337-340, citing Anthony et al., 1994, Clin. Exper. Psychopharmacol. 2:244-268). Large doses of cocaine can provoke cardiac arrest, stroke, and seizure (Hall and Carter, supra, citing Vasica, 2002, Med. J. Austral. 177:260-262; Platt, 1977, Cocaine Addiction: theory, research and treatment, Harvard University Press, Cambridge, Mass.). Further, intravenous administration of cocaine carries the risk of infection by human immunodeficiency virus and various hepatitidies, including hepatitis B and C (Sofuoglu and Kosten, supra citing Booth et al., 2000, Drug Alcohol Dep. 58(3):219-226; Tyndall et al., 2003, Aids 17(6):887-893). Cocaine addiction has been linked to increased crime (Hall and Carter, supra, citing Anglin and Perrochet, 1998, Substance Use and Misure 33:1871-1914). Several years ago the societal cost of cocaine addiction in the United States alone was assessed to be $45 billion dollars, and a theoretical medication that decreased cocaine use by 10 percent was predicted to produce a $745 million dollar economic benefit (Sofuoglu and Kosten, supra citing Cartwright, 2000, Pharmacoeconomics 18(4):405-413).

To date, therapy for addiction has included detoxification and psychosocial treatment, but the relapse rate remains high (Hall and Carter, supra, citing Simpson et al., 1999, Arch. Gen. Psychiatry 56:507-514; Simpson et al., 2002, Arch. Gen. Psychiatry 59:538-544). New options for therapy that are being explored include pharmacologic agents such as dopamine agonists (e.g. disulfiram and amantadine); gamma amino butyric acid ("GABA") enhancers such as tiagabine, baclofen, and topiramate; adrenergic blockers such as propranolol, labetalol, and carvediol; dopamine transport inhibitors such as GBR-12909 and RTI-336; and stimulants such as modafinil and amphetamines including NRP-104 (Sofuoglu and Kosten, supra). Such pharmacologic therapies, however, would generally require consistent compliance on the part of the subject.

As an alternative approach, efforts have been directed toward developing an anti-cocaine vaccine (Sofuoglu and Kosten, supra; Hall and Carter, supra, Montoya, 2008, NIH Public Access manuscript Addiciones, 20(2):111-115; Moreno and Janda, 2009, Pharmaol., Bioche, and Behavior 92:199-205). This approach is somewhat complicated by the fact that the cocaine molecule itself is too small to be immunogenic, and therefore, to be able to function as a vaccine, it must be attached to a larger carrier molecule—together with the carrier, the cocaine acts as a hapten.

Dr. Kim Janda and colleagues developed a potential cocaine vaccine by immunization of cocaine linked via a five carbon linker to Keyhole Limpet Hemocyanin ("KLH"), an immunogenic protein well known as a hapten carrier. Dr. Janda's group also reported the use of an anti-cocaine monoclonal antibody for passive immunization. See Carrera et al., 1995, Nature 378:727-730; Carrera et al., 2000, Proc. Natl. Acad. Sci. U.S.A. 97:6202-6206; Carrera et al., 2001, Proc. Natl. Acad. Sci. U.S.A. 98:1988-1992; Carrera et al., 2004, Bioorg. Med. Chem. 12:563-570; Carrera et al., Proc. Natl. Acad. Sci. U.S.A. 101:10416-10421; and Carrera et al., 2005, 81:709-714.

Dr. Thomas Kosten and his group have developed a potential cocaine vaccine in which succinylnorcocaine is linked to an immunogenic carrier protein derived from cholera B toxin (the "TA-CD" vaccine; Martell et al., 2005, Biol. Psychiatry 58(2):158-164). Clinical trials have shown that a vaccine containing the cholera toxin-cocaine conjugate, especially when administered as five inoculations over a three month period, produced a "robust and dose-related increase in anticocaine antibodies"; however, the antibody levels were observed to decline over time so that, about four months after the original series of inoculations, a booster inoculation is needed (Sofuoglu and Kosten, supra citing Hanet and Kasten, 2004, Expert Rev. Vaccines 3(1):11-18; Kantak et al., 2000, Psychopharmacol. 148(3):251-262; Kasten et al., 2002, Vaccine 20(7-8):1196-1204; Martell et al., 2005, Biol. Psychiatry 58(2):158-164; see also Orson et al., 2008, Ann. N.Y. Acad. Sci. 1141:257-269). Accordingly, because of the need for an initial series of injections and subsequent booster shots, this vaccine, like potential pharmaceutical therapies, requires a substantial level of commitment on the part of the subject.

As another example of a potential vaccine, Fox et al. (1996, Nature Medicine 2(10):1129-1132; Kantak et al., 2000, Psychopharmacol. 148:251-262) report that vaccination of mice with cocaine conjugated to immunogenic bovine serum albumin ("BSA") produced a long-lasting antibody response. Mice immunized with cocaine-BSA were reported to exhibit altered cocaine pharmacokinetics. A monoclonal anti-cocaine antibody was generated which, when administered to rats, was observed to reduce self-administration of cocaine.

Hrafnkelsdottir et al. (2005, Biol. Pharm. Bull. 28(6): 1038-1042) report induction of protective and specific antibodies against cocaine in mice immunized with an intranasal cocaine vaccine containing cocaine conjugated to KLH and the mucosal adjuvant, macrogol-6-glycerol capylocaprate ("RhinoVax"). Nasal administration was observed to confer a beneficial mucosal immunity.

Disadvantages of these vaccine approaches include (i) use of an immunogenic carrier protein would result in an undesirable extraneous immune response to the carrier itself, (ii) use of long tethers to link a hapten to a carrier protein could result in formation of a number of neo-epitopes which, in turn, could "dilute" the specific immune response to a hapten, and (iii) maintenance of antibody levels would require the administration of periodic booster vaccinations.

Deng et al., 2002, Proc. Natl. Acad. Sci. U.S.A. 99(6): 3412-3416 showed that cocaine covalently modifies plasma proteins in vivo forming a benzoyl ecgonine ("BE") amide hapten through lysine $\epsilon$-amino groups of plasma proteins such as albumin (see FIG. 1). They showed the presence of such cocaine conjugates in plasma of rats and human subjects chronically exposed to cocaine. Further, it was found that when the benzoyl ecgonine N-hydroxysuccinimide ester of cocaine was administered directly to mice, plasma proteins were conjugated to cocaine in vivo and mice developed anti-cocaine antibodies, indicating that the proteins conjugated in vivo were immunogenic. Deng et al. also showed that anti-cocaine antibodies were detected in some long-term cocaine users.

Various other publications and patents that relate to anti-drug vaccines and antibodies include U.S. Pat. No. 6,699,474 (drug conjugated to carrier such as KLH); Kinsey et al., 2009, Immunology and Cell Biology 87: 309-314 (review of anti-drug vaccines); U.S. Pat. Nos. 7,452,541 and 6,932,971 (hapten conjugated to protein carrier in a repetitive array); Hardin et al, 1998, J Pharmacol Exp Ther 285:1113-1122 and Proksch et al., 2000, J. Pharmacol Exp Ther. 292:831-837 (antibodies toward phencyclidine (PCP) reduce PCP levels in the brain); Byrnes-Blake et al., 2001, Int Immunopharmacol 1:329-338 (antibodies to methamphetamine); U.S. Pat. No. 5,256,409 (vaccine comprising a carrier protein bound to one hapten from the desipramine/imipramine class and another hapten from the nortriptyline/amitriptyline class of drugs); Carrera et al., 1995, Nature 379:727-730; WO 92/03163; U.S. Pat. No. 6,383,490 (anti-cocaine antibodies; cocaine/carrier conjugates; importance of linker in joining cocaine to carrier); Landry et al., 1993, Science 259:1899-1901 and WO 93/20076 (immunization with transition state analogues of cocaine to produce catalytic antibodies that inactivate cocaine); Spector, et al., 1973, Pharmacol. Rev. 25:281-291 and Berkowitz et al., 1982, Science 178:1290-1292 (anti-morphine antibodies); Bagasra, et al., 1992, Immunopharmacol. 23:173-179 and Gallacher, 1994, Immunopharmacol 27:79-81 (cocaine/carrier conjugates; anti-cocaine antibodies); Killian et al., 1978, Pharmacol. Biochem. Behavior 9:347-352 and Pentel et al., 1991, Drug Met. Dispositions 19:24-28 (passive immunization against drugs); EP 0 613 899 A2 (cocaine/protein conjugate; anti-cocaine antibodies); U.S. Pat. Nos. 3,888,866 and 4,123,431 (cocaine/protein conjugates; anti-cocaine antibodies); WO 93/12111 (cocaine/protein conjugates); U.S. Pat. Nos. 4,620,977, 4,813,924, 4,834,973; and 5,037,645 (drug/protein conjugates); and U.S. Pat. No. 6,054,127 (drug/carrier conjugates where carrier is immunogenic; cocaine/carrier conjugates).

3. SUMMARY OF THE INVENTION

The present invention relates to anti-drug vaccines and methods for their use. It is based, at least in part, on the discovery that cocaine/protein conjugates may be formed in vitro that resemble those formed in vivo. Although it is known that use of cocaine results in in vivo conjugation of cocaine to serum proteins, the level of such proteins is low. Some long-term cocaine users have been found to have anti-cocaine antibodies, but the level (titers) of such antibodies is usually low and they are mostly of low affinity antibody class IgM. These antibodies have apparently not been sufficient to deter the subject from use of the drug.

Prior attempts to produce an anti-cocaine vaccine have linked cocaine to an immunogenic carrier molecule. The present invention offers, for the first time, Self-proteins (proteins which are not immunogenic in the host) conjugated to cocaine which may be administered in an amount and according to a schedule to produce therapeutic immunity against cocaine, where antibodies are generated at levels to blunt the effects of cocaine and discourage further use. Moreover, according to certain embodiments of the invention, if a subject previously immunized against cocaine linked to an endogenous Self protein were to decide to use cocaine again after immunization, exposure to cocaine would generate cocaine-Self protein conjugates which would resemble or duplicate the cocaine-Self protein originally used to immunize the subject The result would effectively be an automatic booster inoculation triggered by relapse of cocaine abuse.

The present invention is described primarily in the context of haptenizing cocaine, but may also be applied to other drugs where it is desirable to discourage the use of the drug or it is desirable to decrease the biological effect of the drug. Non-limiting examples of such drugs would include nicotine, phencyclidine, heroin and opioids.

In a first set of embodiments, the present invention provides for an isolated conjugate between a "Self" protein and a drug which preferably either lacks a tether between the two or has a tether which is sufficiently small so that it is essentially non-immunogenic. A "Self" protein is more fully defined below, and may preferably be an endogenous protein (naturally found in a subject to be vaccinated) but more generally may be any non-immunogenic protein. The use of a Self protein as carrier avoids an irrelevant immune response to the carrier itself. Because, preferably, a tether is absent or small, the likelihood of generating antibodies to the tether region is absent or low, respectively.

In a second set of embodiments, the present invention provides for a pharmaceutical composition comprising an immunogenic amount (when introduced into a subject) of a conjugate between a "Self" protein and a drug which preferably either lacks a tether between the two or has a tether which is sufficiently small so that it is essentially non-immunogenic.

In a third set of embodiments, the present invention provides for a method of treating a subject to diminish (decrease, inhibit) the subject's response to and/or use of a drug, comprising administering, to the subject, a pharmaceutical composition comprising an immunogenic amount of a conjugate between a "Self" protein and the drug which preferably either lacks a tether between the two or has a tether which is sufficiently small so that it is essentially non-immunogenic.

4. BRIEF DESCRIPTION OF THE FIGURES

FIG. 1A-B. (A) Nucleophile transfer to cocaine yielding BE acylation product. (B) Controlled synthesis of 0-tether conjugate.

FIG. 2. Examples of cocaine/Self protein conjugates.

Figure 3B:
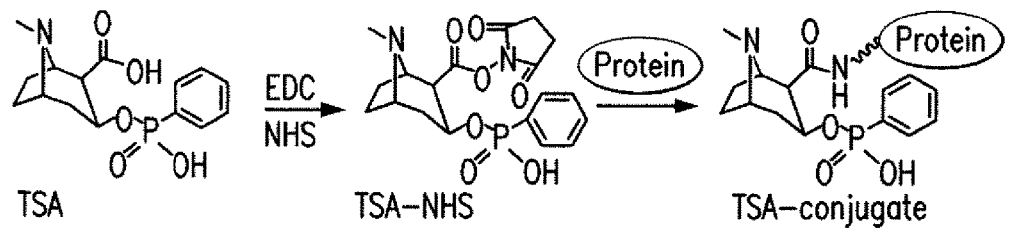
Figure 3C:
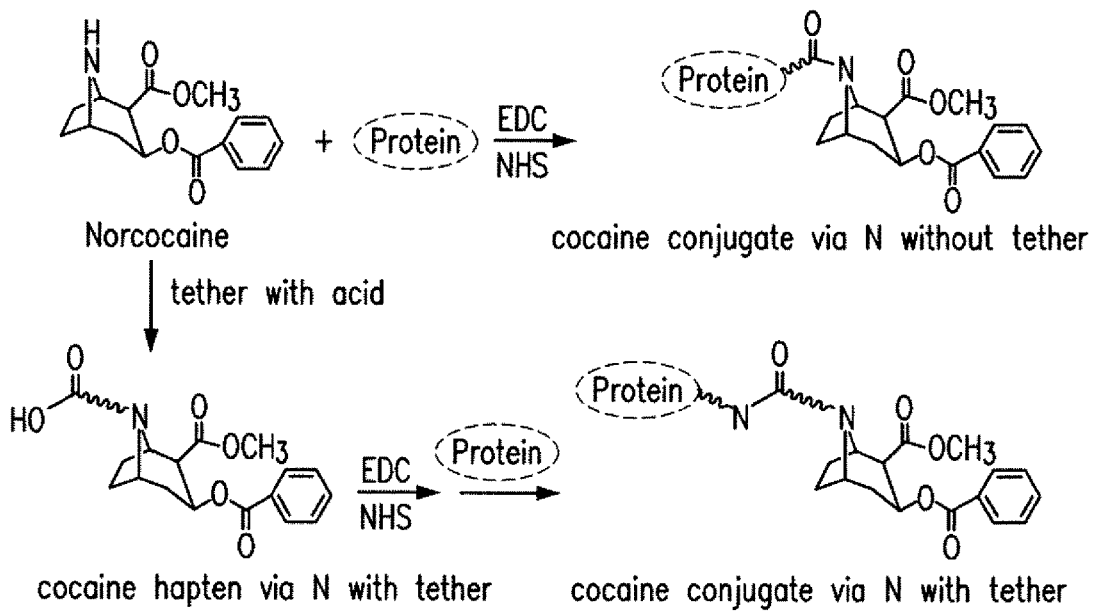

FIGS. 3A-C. Synthetic schemes for producing cocaine/Self protein conjugates starting with either (A) benzoyl ecgonine; (B) a transition state analog ("TSA"); or (C)

norcocaine. NHS is N-hydroxysuccinimide. EDC is ethyl 3-(3-dimethylaminopropyl)-carbodiimide FIG. 4. Results of screening for human monoclonal anti-cocaine antibodies.

Figure 5A:
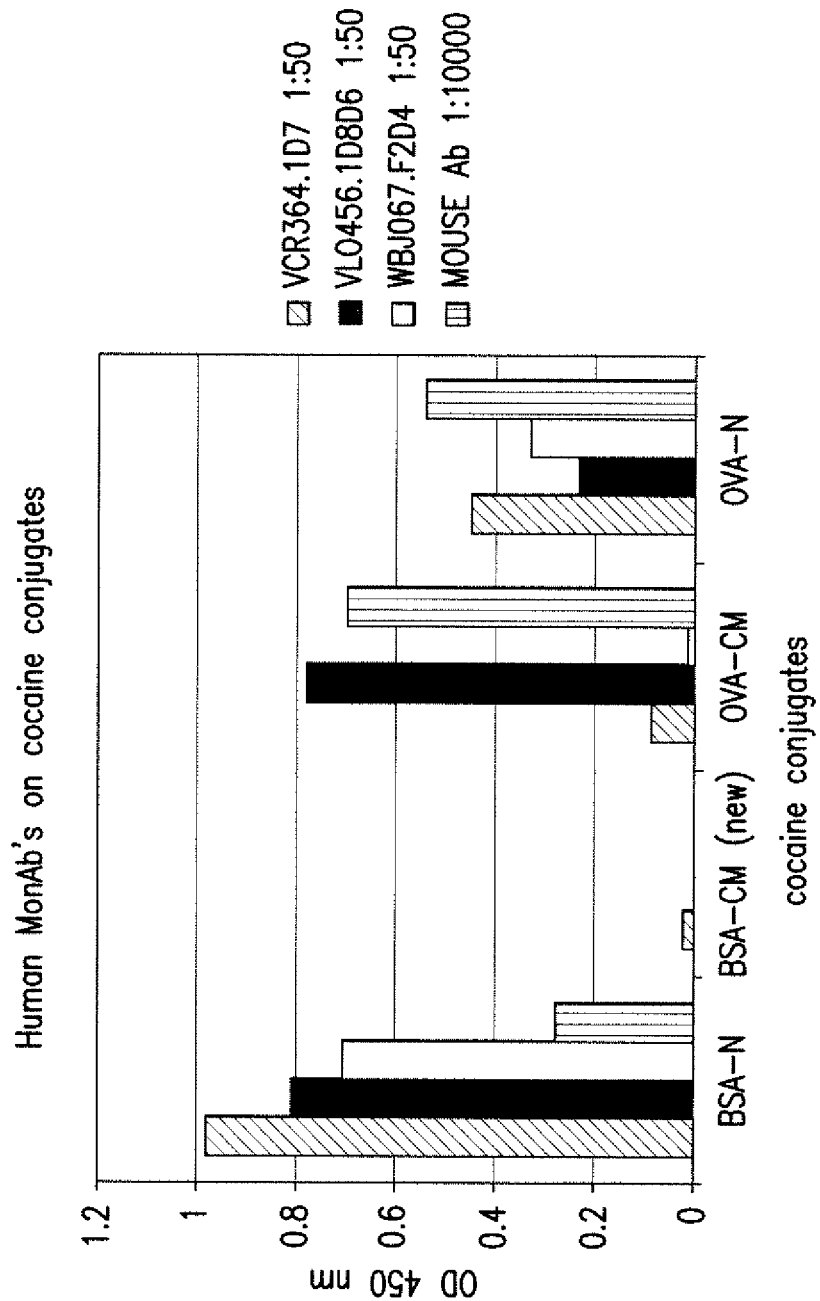
Figure 5B:
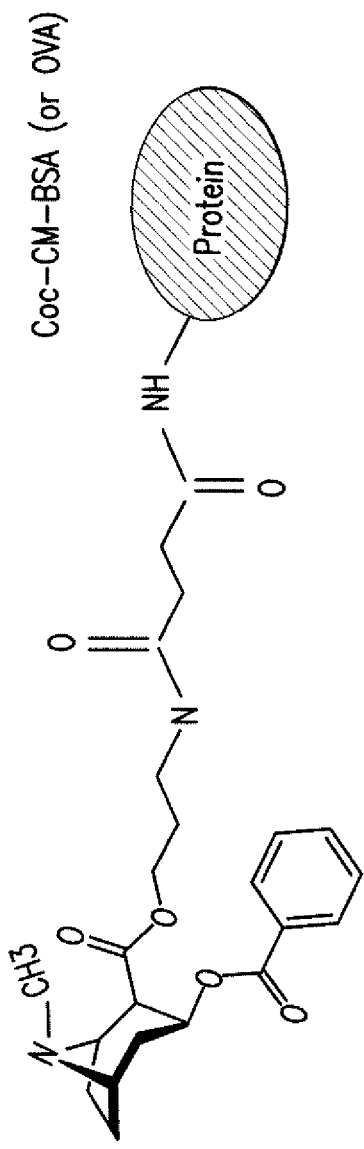
Figure 5C:
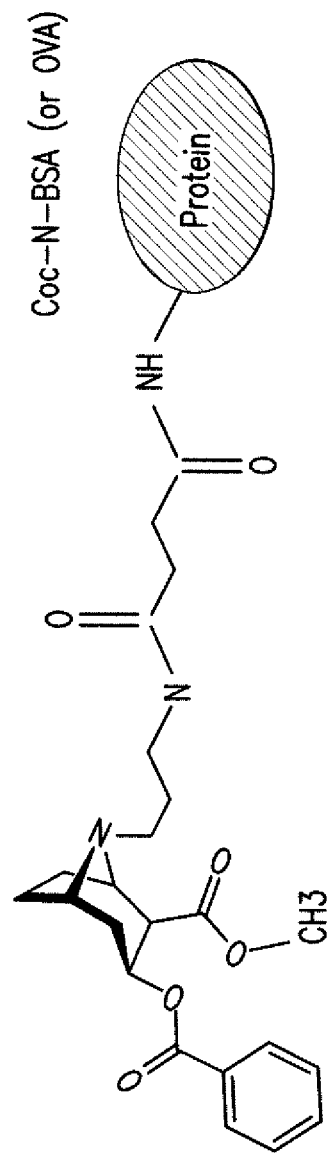

FIG. 5A-C. (A) Results of human hybridoma screening for binding of monoclonal antibodies to cocaine conjugated to bovine serum albumin ("BSA") or ovalbumin ("OVA"). Cocaine was conjugated either to (B) the N of the tropane group (indicated by "N") or (C) as a benzoyl ecgonine ester (indicated by "CM").

Figure 6A:
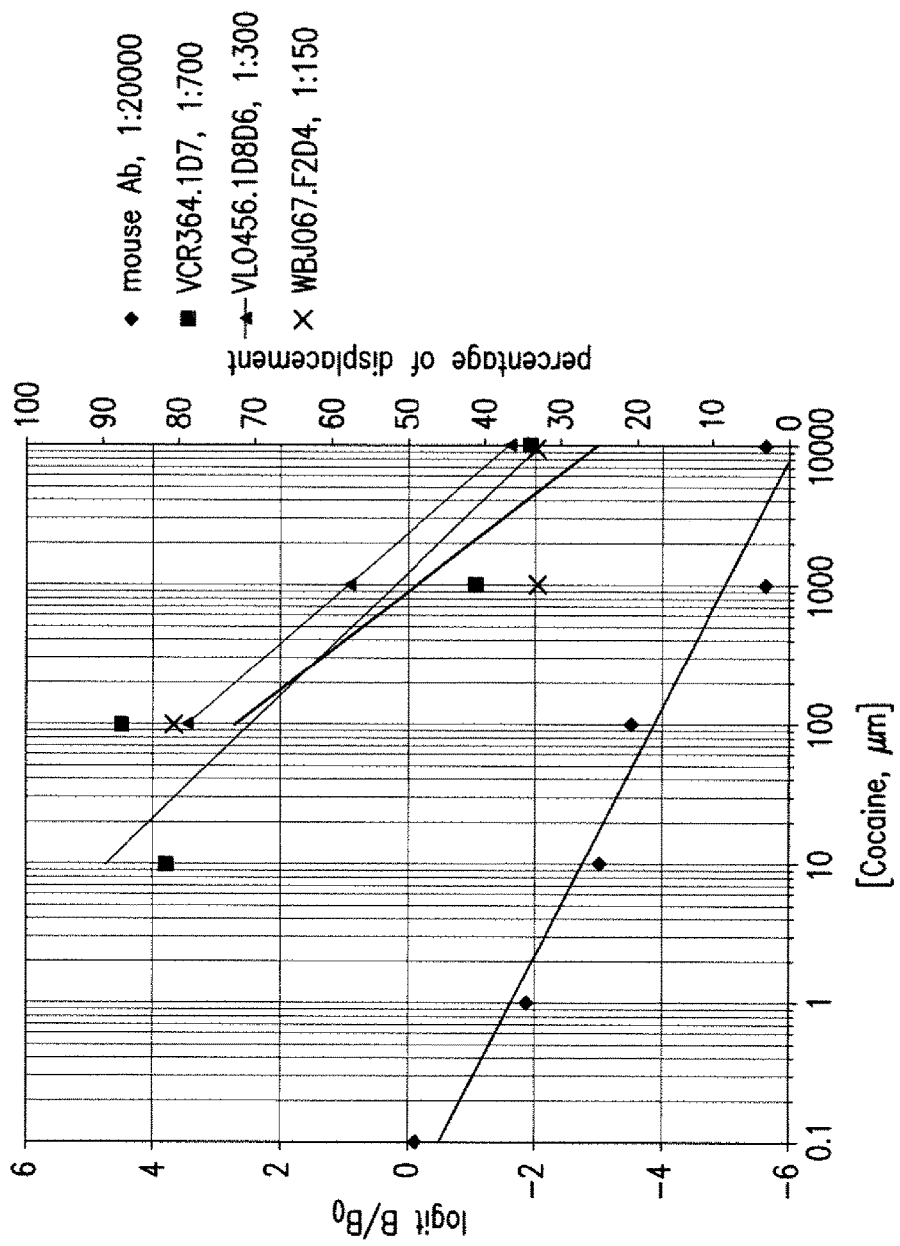
Figure 6B:
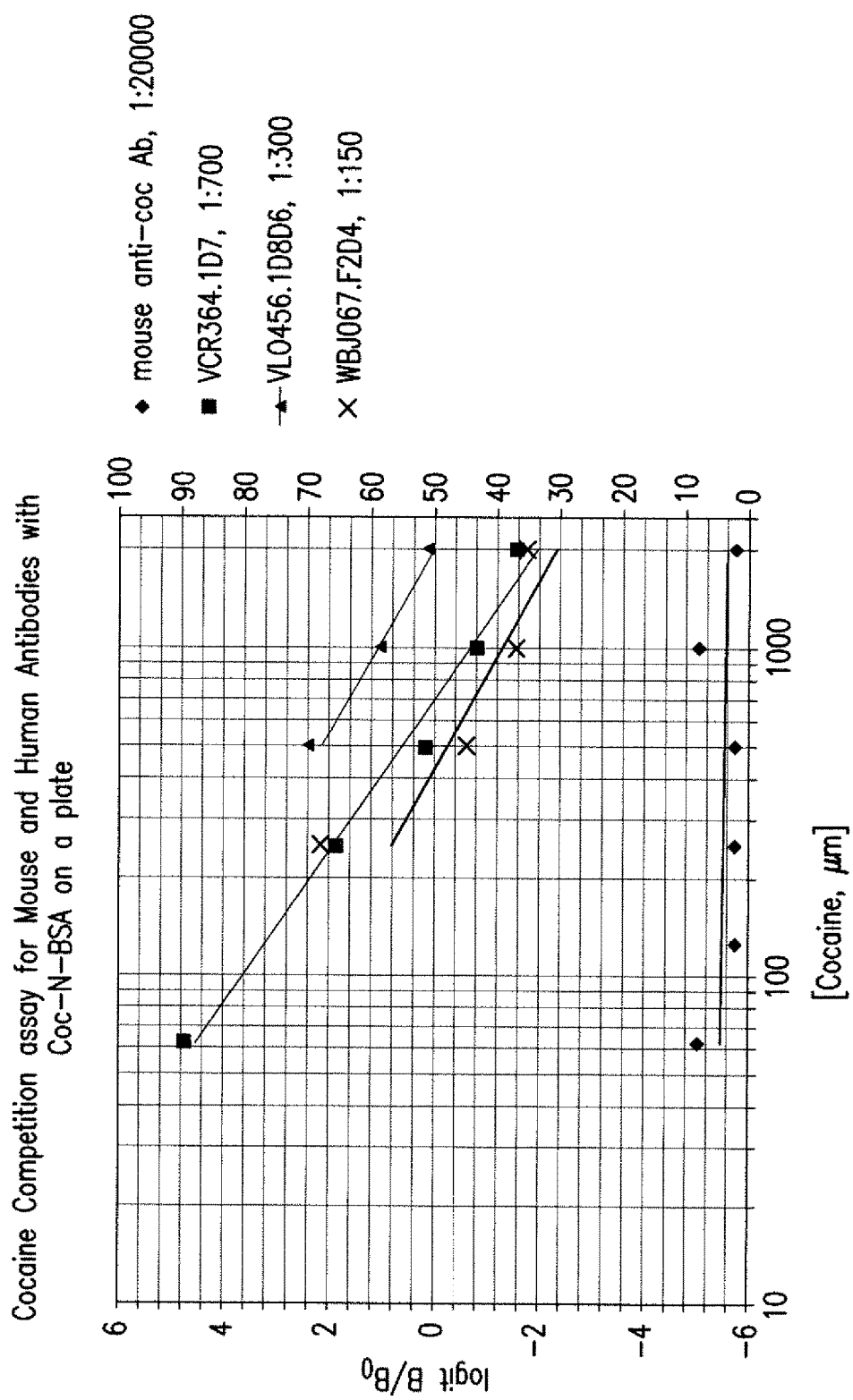
Figure 6C:
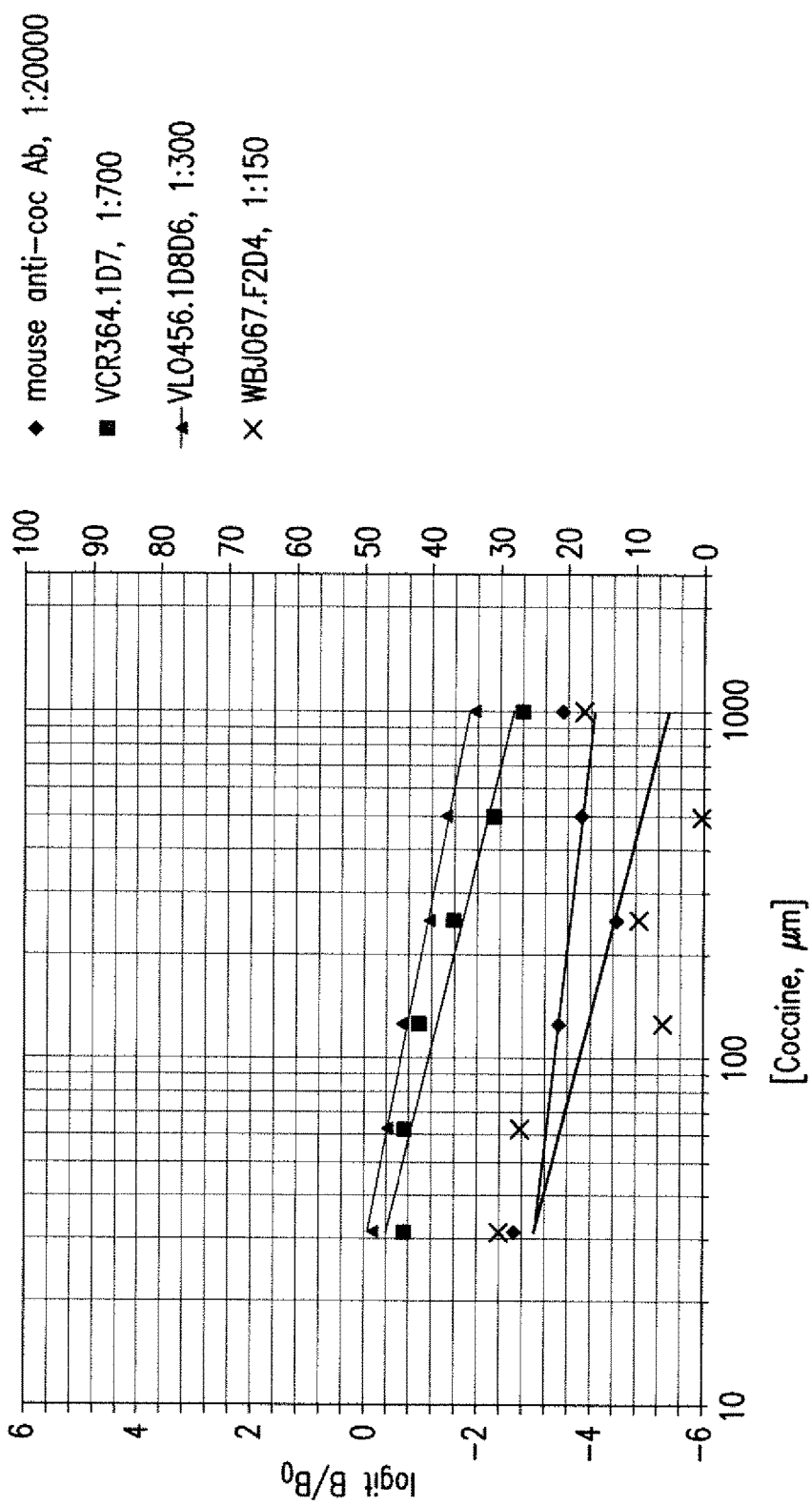

FIG. 6A-C. (A,B) Cocaine competition assay for mouse and human antibodies with Cocaine-BSA-N on a plate. Unless indicated differently, mouse antibody used in these experiments was monoclonal antibody against benzoyl ecgonine supplied from RayBiotech Inc., GA, USA. (B) shows a larger scale of competitor (cocaine) concentration than (A). (C) Cocaine-N-BSA competition assay for mouse and human antibodies with cocaine-BSA-N on the plate.

Figures 7A, 7B, 7C:
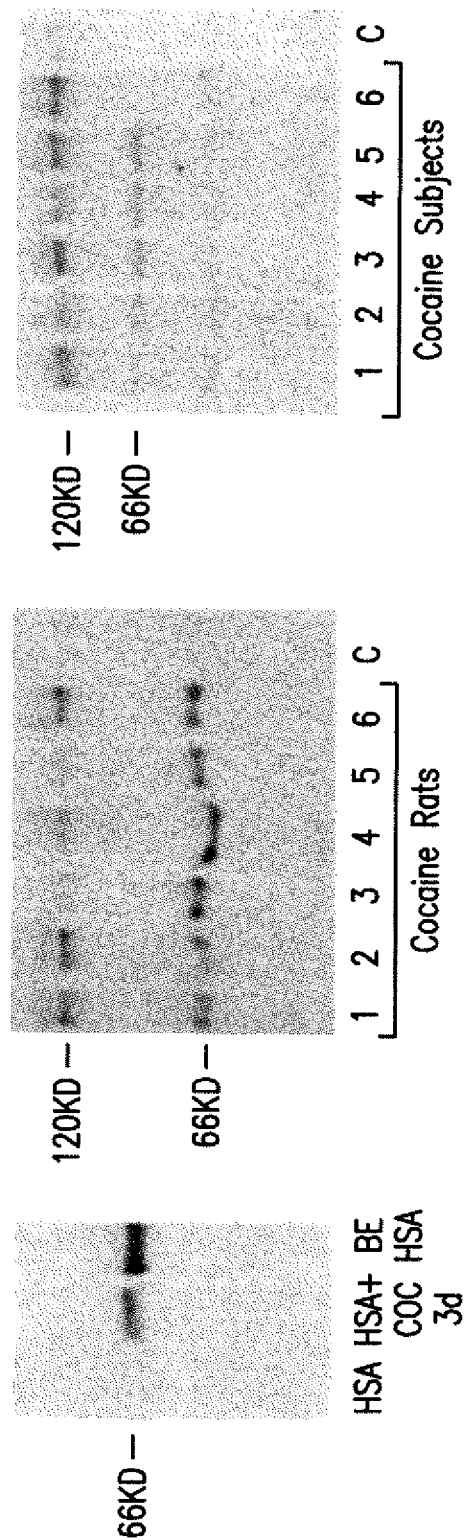

FIG. 7A-C. Western blots between labeled mouse monoclonal anti-cocaine antibody 46H1 and PAGE-separated protein blots as follows: (A) HSA (control); HSA incubated with cocaine for 3 days, and benzoyl ecgonine-linked HSA; (B) serum proteins of rats that had been treated with cocaine (or untreated control C); and (C) serum proteins of human cocaine users (or normal control C).

FIG. 8A-D. Binding of various dilutions of monoclonal antibodies (A) fully human 1D8D6; (B) fully human 1D7; (C) fully human F2D4 or (D) murine anti-cocaine monoclonal antibody to either Coc-HSA 1, Coc-HSA-2, Coc-HSA-3, Coc-HSA 4, or Coc-N-BSA. Coc-HSA 1, Coc-HSA 2 etc. are different batches of Cocaine-HSA conjugates stored for different periods of time. Coc-N-BSA is a cocaine BSA conjugate, where cocaine is coupled through tropane's N. By testing different batches of Coc-HSA it was determined that batch 3 had the best binding pattern which means that cocaine was preserved in this batch in its original hapten form as benzoyl ecgonine.

Figure 9:
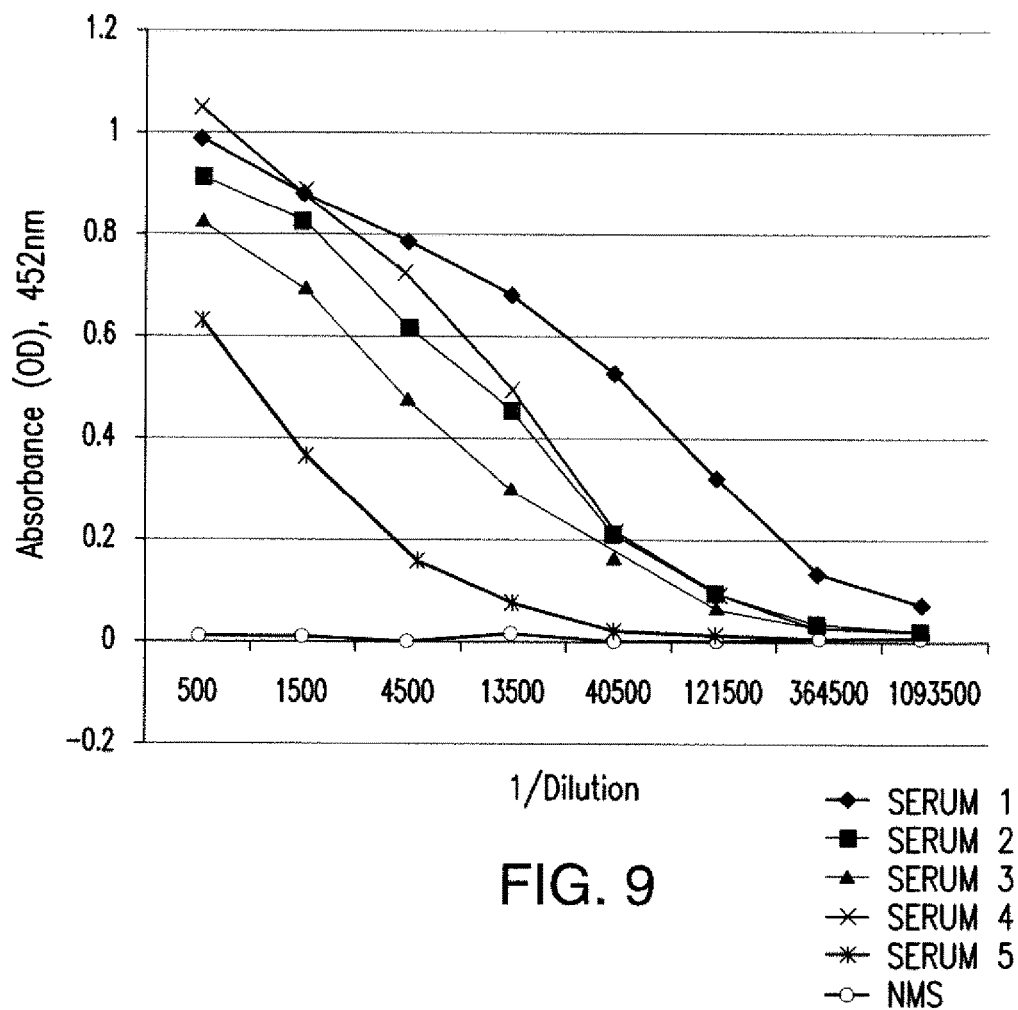

FIG. 9. Titration of sera from mice immunized with MSA-O-tether-cocaine (MSA-0-tet-Coc or MSA-coc) as an antigen in ELBA.

Figure 10:
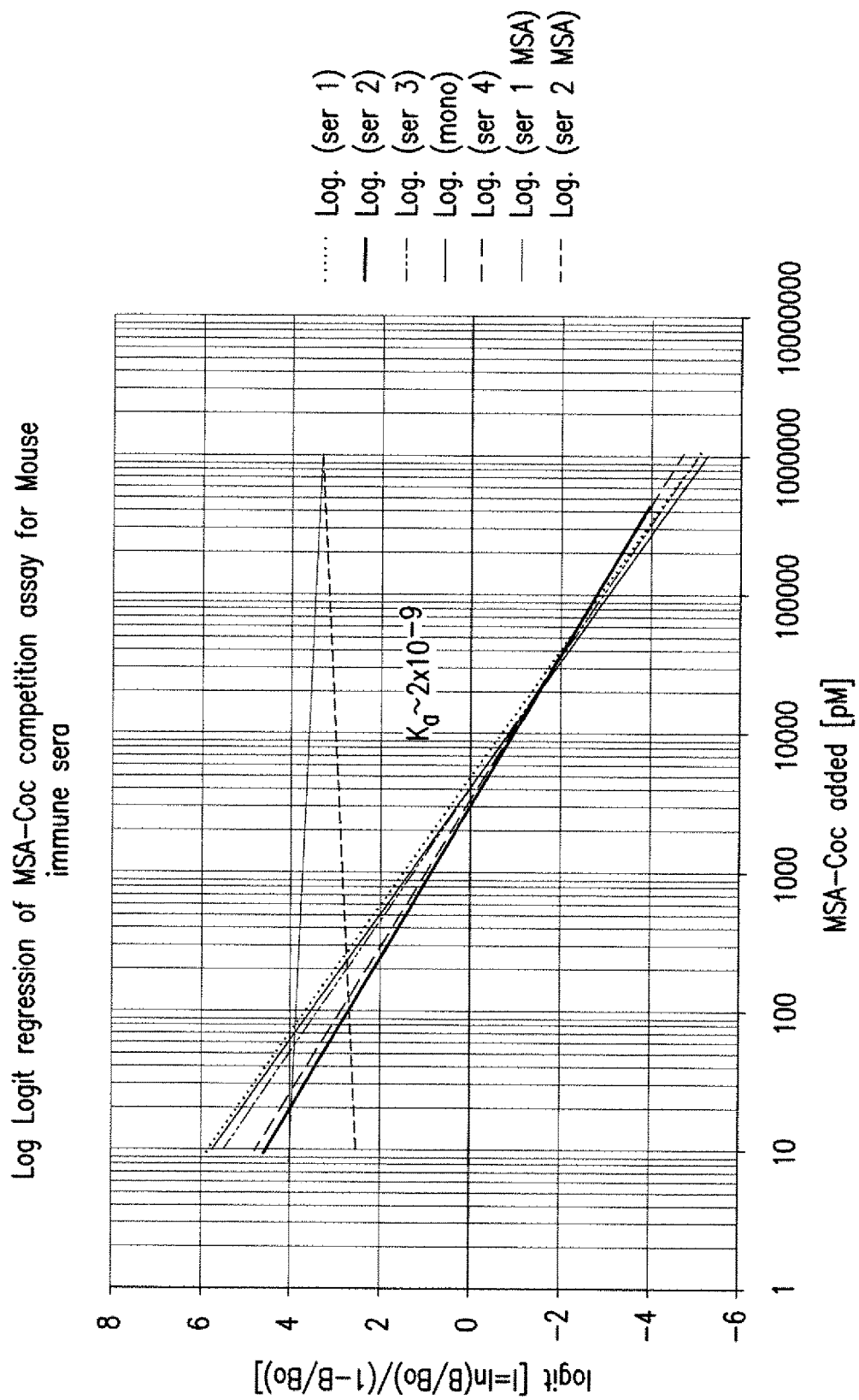

FIG. 10. Log-Logit regression of competition assay for mouse immune sera using MSA-O-tet-Coc as a competitor.

Figure 11:
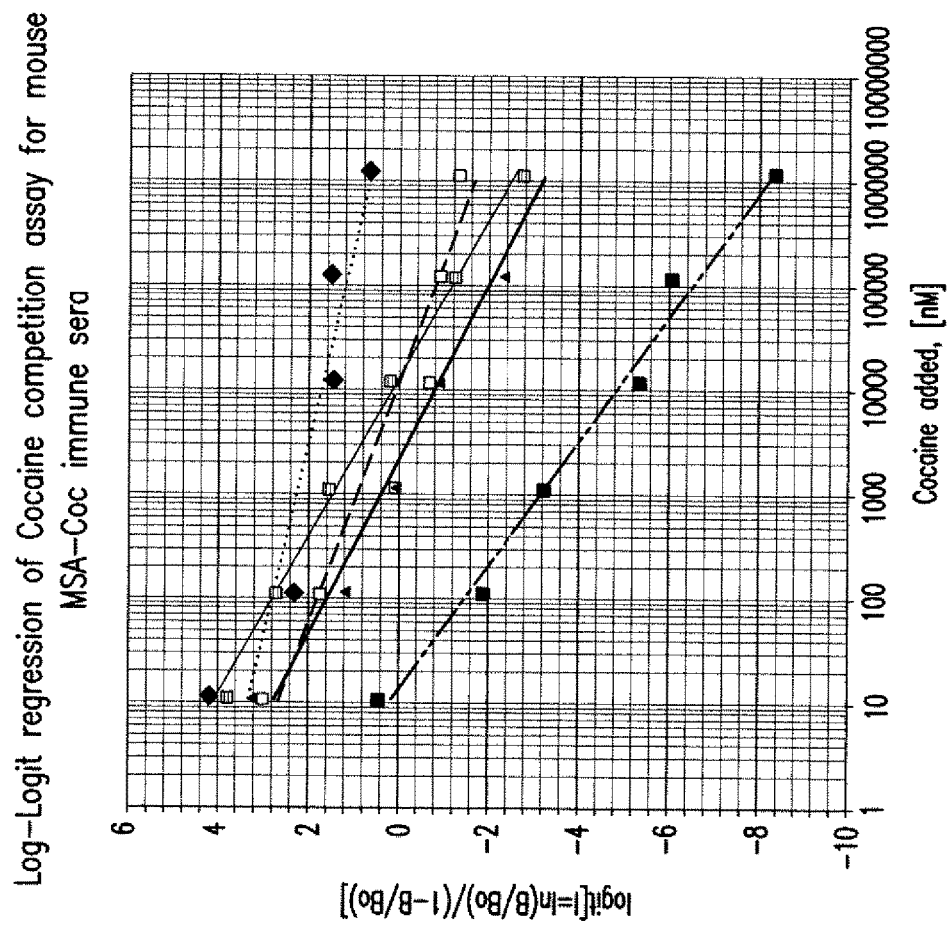

FIG. 11. Log-Logit regression of competition assay for mouse immune sera using cocaine as a competitor.

Figure 12:
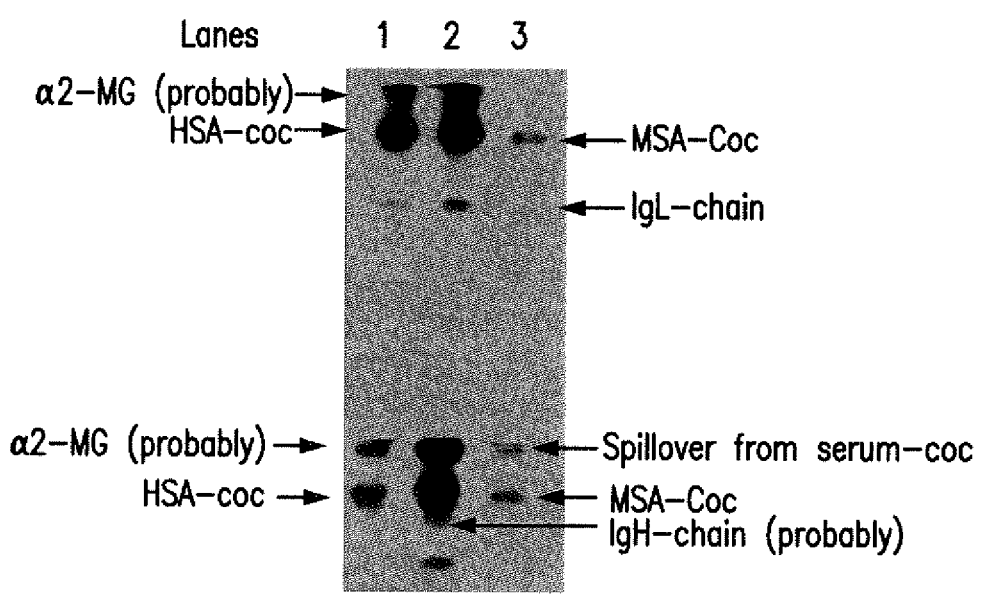

FIG. 12. Western blotting of MSA and human serum protein conjugates through O-tether to cocaine using mouse monoclonal benzoyl ecgonine specific antibody.

Figure 13:
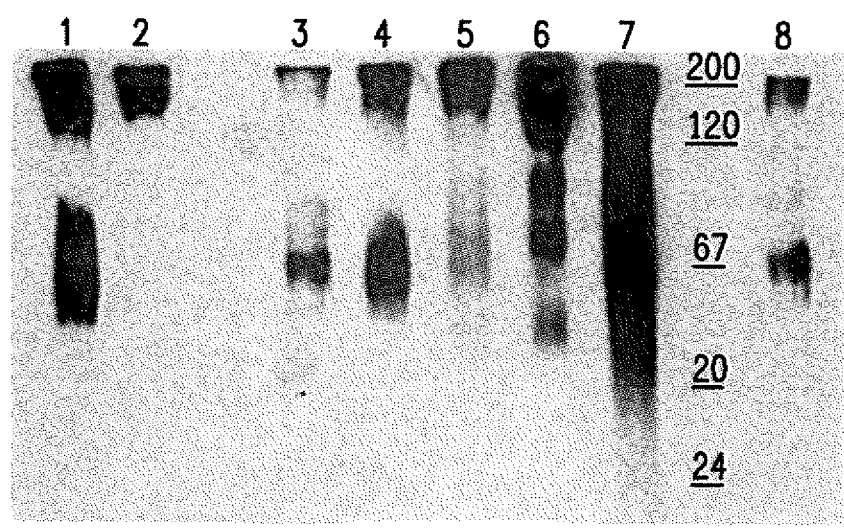

FIG. 13. Western blot of: RSA-coc (1), mIg-coc (2), MSA-coc (3), HSA-coc (4), mTSP-coc (5), mIg-coc (6), mouse serum (7) and GSA-coc (8).

Figure 14B:
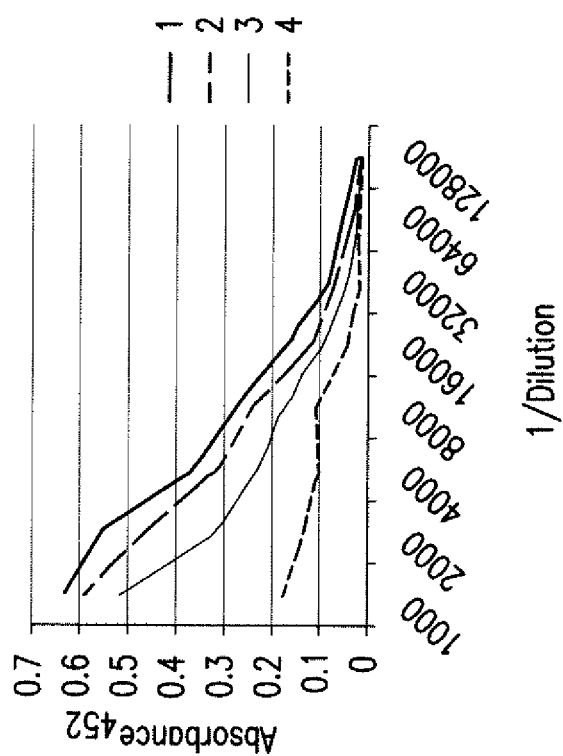
Figure 14A:
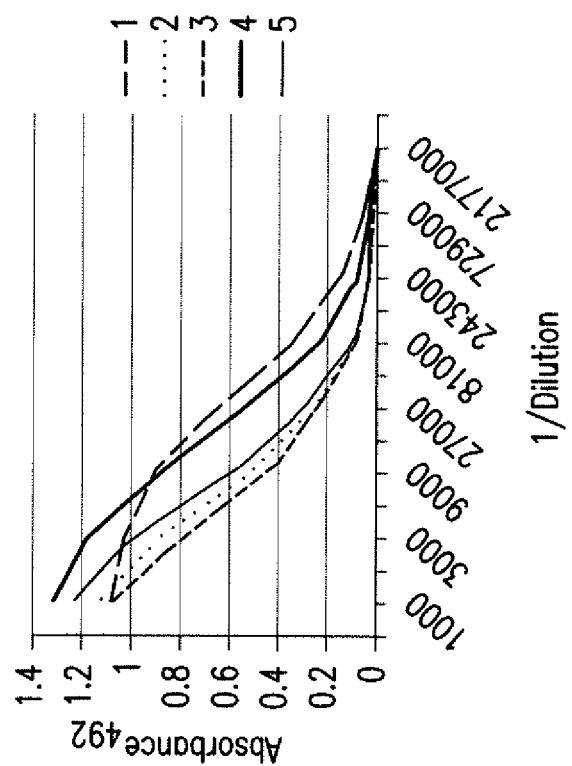

FIGS. 14A-B. ELISA of anti-coc antibodies generated upon vaccination of mice with (A) MSA-coc and (B) mIG-coc; absorbance (492 nM) represents titers of antibodies.

Figure 15:
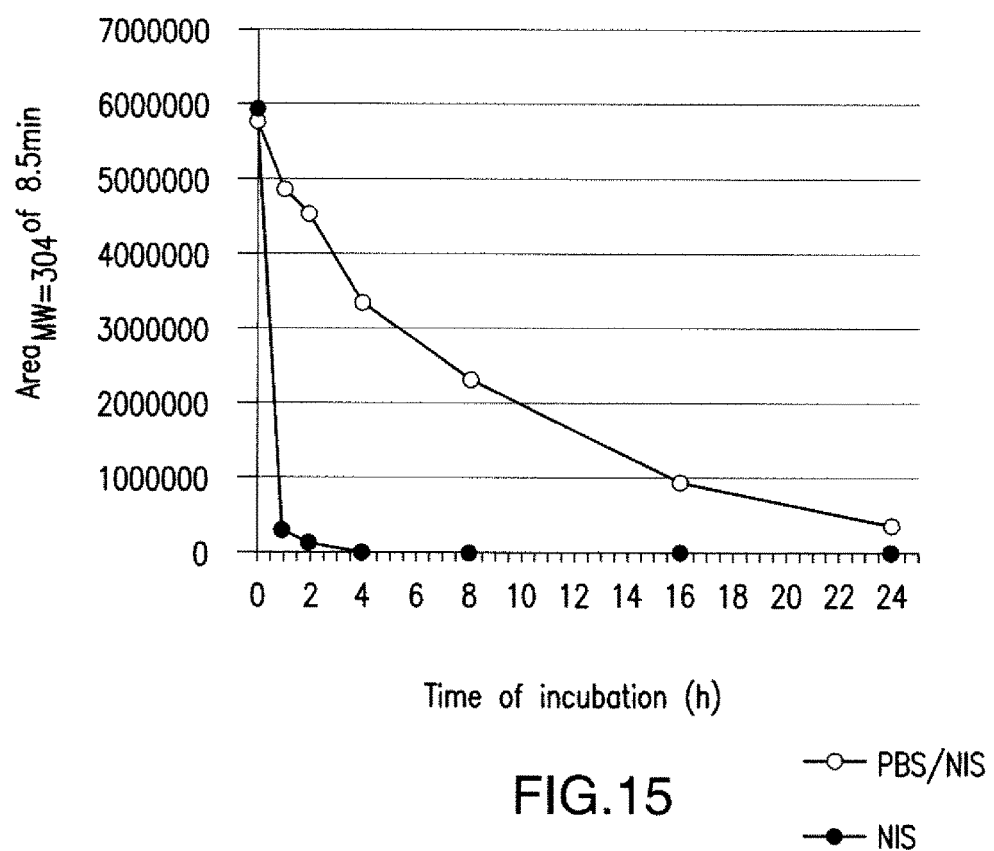

FIG. 15. Degradation of cocaine in non-immune mouse serum (NIS) and in non-immune mouse serum diluted in PBS (PBS/NIS) by mass spectrometry.

Figures 16A, 16B:
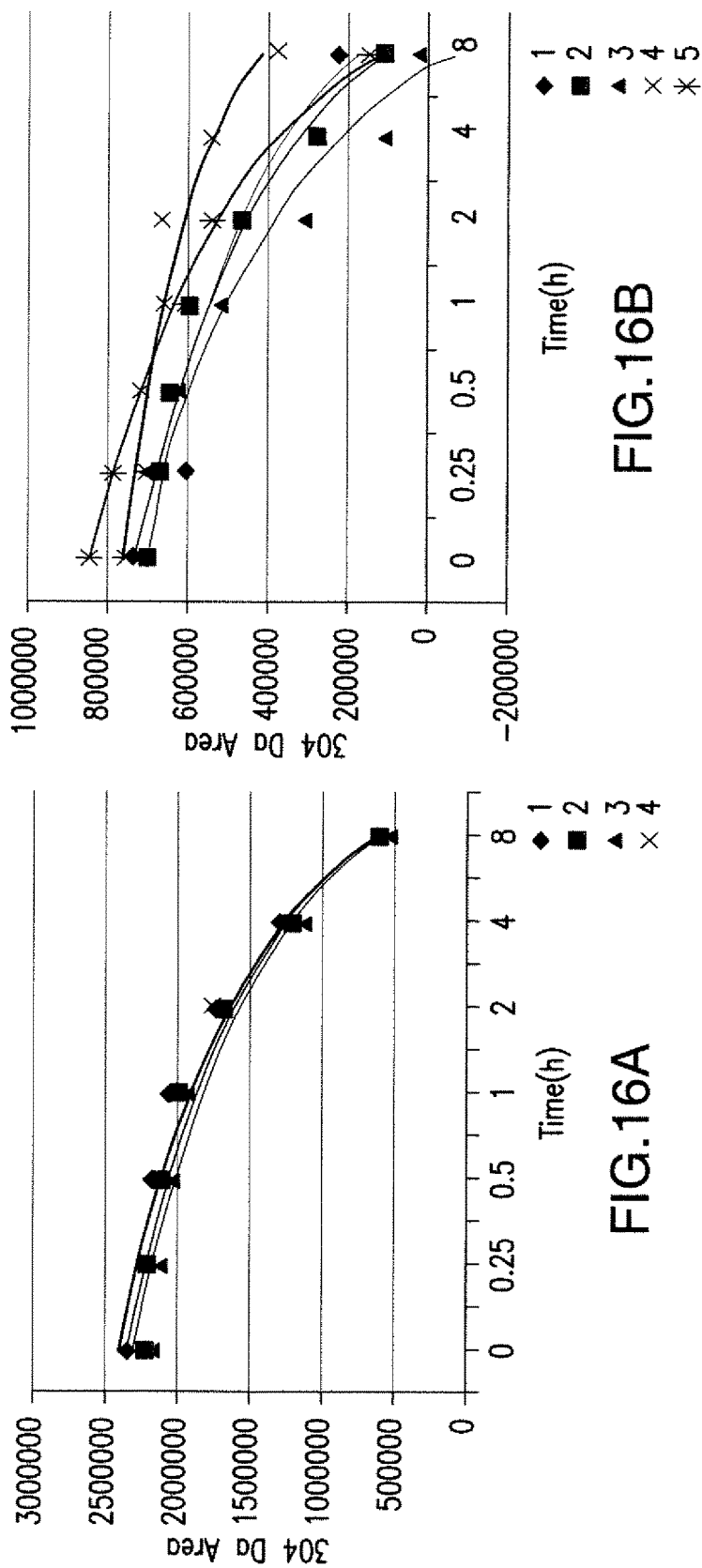

FIGS. 16A-B. Rates of cocaine degradation in (A) non-immune mouse sera and (B) 5 immune mouse sera measured by a decrease in peak area (y-axis) of the cocaine peak generated by mass-spectrometry analysis.

Figure 17:
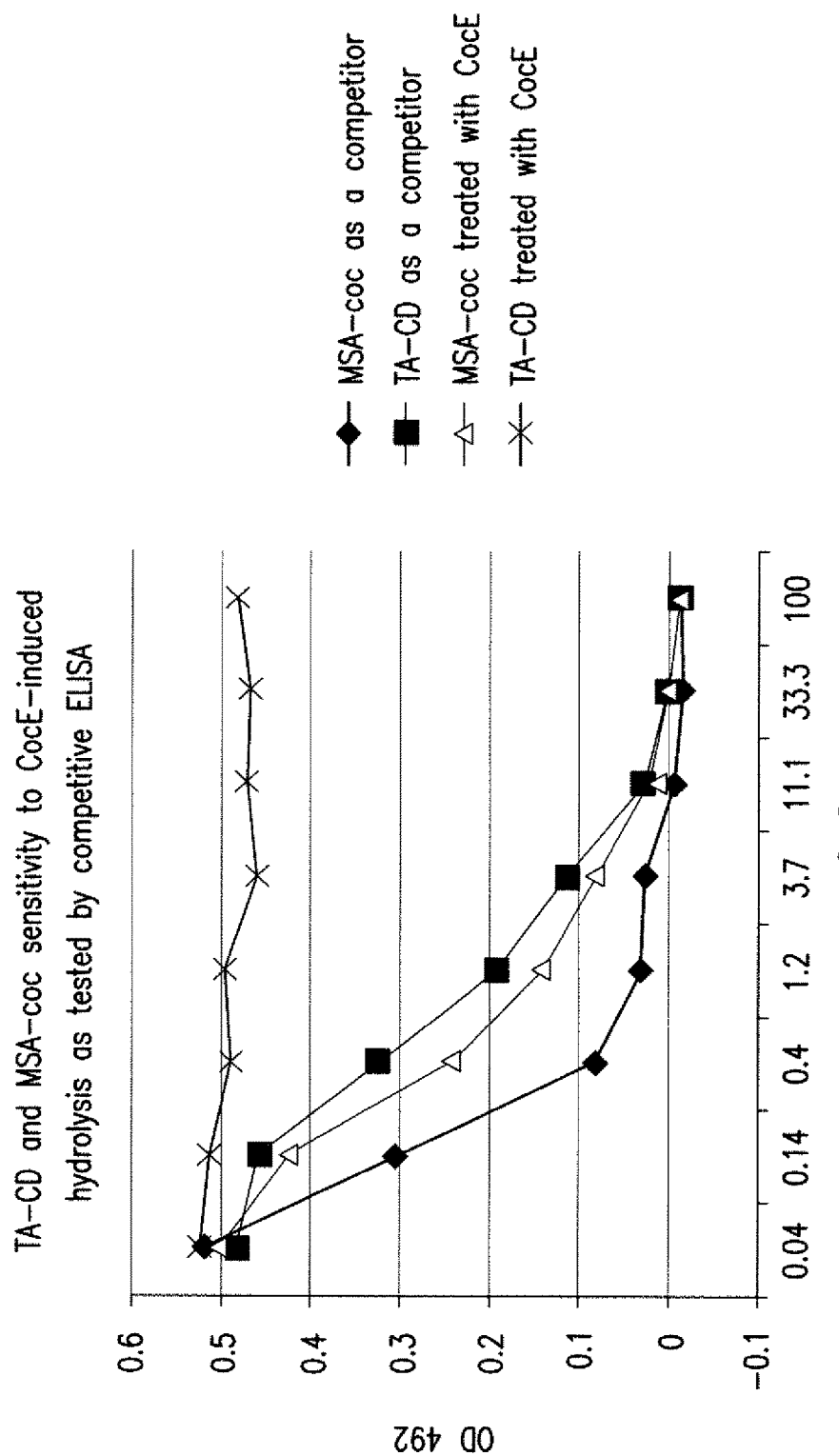

FIG. 17. Competition of tethered and 0-tethered cocaine conjugates treated and non-treated with CocE. Antigen on a plate is OVA-coc. Immune serum from mice immunized with MSA-coc was used as a source of antibodies.

FIGS. 18A-B. Comparison of (A) TA-CD (immunogenic carrier, tether) with (B) one embodiment of the present immunoconjugate vaccine (zero-tether, self-protein).

5. DETAILED DESCRIPTION OF THE INVENTION

The present invention provides for an isolated conjugate between a "Self" protein carrier and a drug which preferably either lacks a tether between the two or has a tether which is sufficiently small so that it is essentially non-immunogenic. The present invention also provides for pharmaceutical compositions comprising said conjugate and their use in the treatment of drug abuse, dependence, overdose and/or addiction. Although the description primarily relates to cocaine, by modifying the chemistry according to the knowledge of a skilled artisan, analogous conjugates between Self protein and other drugs, including but not limited to nicotine, phencyclidine, opioids, or heroin, may be prepared and used in parallel pharmaceutical compositions and methods to treat addiction to these substances.

"Cocaine" includes cocaine and derivatives thereof, including TSA (transition state analogs) which, when bound to Self protein carrier and injected into an immunocompetent host (where said carrier is a Self protein in the host) are capable of inducing antibody directed to free cocaine and to cocaine bound to carrier.

An immunocompetent host is a host animal which responds to an antigenic stimulus by mounting an antibody-based and preferably also a cell-based immune response. As one specific non-limiting example, an immunocompetent host mounts an immune reaction against KLH. Another specific, non-limiting example is an immunocompetent host that mounts an immune reaction to cholera toxin B-chain. In both examples, the antigen is a non-Self protein immunogen. It is understood that some human subjects who would benefit from an anti-drug vaccine may manifest decreased immunity relative to other members of the population, however, if such persons do mount an immune response including antibody production, albeit at decreased levels relative to control subjects, they are still considered immunocompetent herein.

A "Self" protein is any protein that is not immunogenic—that is to say, does not provoke a substantial immune response—when introduced into an immunocompetent subject, i.e., it would not be recognized as foreign by the immune system of an immunocompetent subject to which it is administered. In particular non-limiting embodiments of the invention, a Self protein is a protein naturally found in a subject to be vaccinated (an endogenous protein). Alternatively, a Self protein may be a protein that resembles an endogenous protein but is not identical to it, yet nevertheless does not provoke a substantial immune response. Whether a protein qualifies as a Self protein depends to at least some extent on the identity of the intended subject to which it is administered; for example, human serum albumin ("HSA") is a Self protein to a human but is not a Self protein to a mouse. The term "protein" as used herein refers to a molecule that comprises amino acids and peptide bonds, and includes, within its scope, unmodified as well as modified proteins, glycoproteins, proteins conjugated to one or a plurality of non-protein/non-amino acid molecules, proteins comprising at least a portion of non-naturally occurring amino acids, proteins conjugated to one or more polyalkylene oxide molecule (e.g., pegylated protein), etc. Non-limiting examples of human Self proteins which may be used as carrier proteins are HSA, human alpha 2 macroglobulin, human immunoglobulin, especially human immunoglobulin constant and framework regions, pegylated allogeneic human protein or pegylated non-human protein, etc. For illustration, examples of non Self-protein for humans include KLH, endotoxin, exotoxin, cholera toxin, bovine thyroglobulin, ovalbumin, and tetanus toxoid. Non-limiting examples of mouse Self proteins which may be used as carrier proteins include mouse serum albumin ("MSA"), mouse alpha 2-macroglobulin, and mouse immunoglobulin, especially mouse immunoglobulin constant and framework regions.

A tether, if present, is a molecular bridge that joins cocaine to the Self protein carrier (it may originate as part of a "cocaine hapten", see below). As such, the tether does not constitute, in whole or in part, an element of either the hapten itself or the carrier (although hapten and/or carrier may be modified to facilitate linkage to the tether (e.g. in a "pre-hapten"; see below)). In preferred embodiments, the tether is sufficiently small so that it does not provoke a substantial immune reaction in an immunocompetent host. In particular, non-limiting embodiments of the invention, the tether, if present, comprises one or more carbon ("C") atom, optionally linked to another species of atom such as, but not limited to, hydrogen, oxygen, and/or nitrogen; for example, the tether, where present, may comprise 1-4 and preferably 1-2 carbon atoms. Preferably, the hapten is linked to carrier via what is termed a "0-tether", which means direct coupling (linkage) of hapten to a carrier protein without the incorporation of an independent linker.

For clarity of description and not by way of limitation, the detailed description of the invention is divided into the following subsections:
(i) cocaine pre-haptens;
(ii) preparation of drug/Self protein conjugates;
(iii) pharmaceutical compositions; and
(iv) methods of use.

5.1 Cocaine Pre-Haptens

A cocaine pre-hapten is a molecule which is reacted with a carrier Self protein to form a cocaine hapten/Self protein carrier conjugate (also referred to herein as a cocaine/Self protein or cocaine/protein or cocaine/carrier conjugate), optionally joined by a tether. Where a tether is intended, the cocaine pre-hapten preferably comprises a molecular structure that, when reacted with Self protein, creates the tether, although it is possible that a synthesis may be designed so that the tether is provided by an additional reactant.

Formula I, below, is the structure of cocaine:

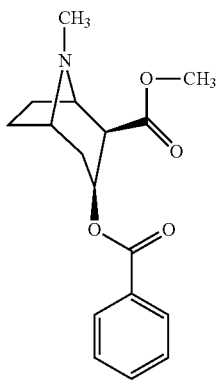 [SMILES: COC(=O)[C@@H]1C2CCC(C[C@@H]1OC(=O)c1ccccc1)N2C]

Formula II, below, is the structure of a cocaine pre-hapten:

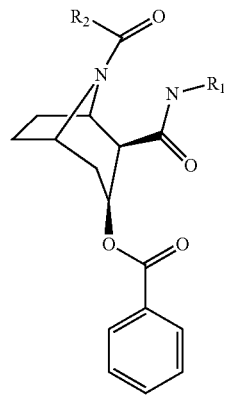

wherein $R_1$ and $R_2$ are the same or different, and may be:

unsubstituted or substituted, branched or unbranched, alkyl (preferably $C_1$-$C_4$ or $C_1$-$C_2$ alkyl) where one or more substituent may be hydroxyl (OH) or a ketone (=O); or unsubstituted or substituted, branched or unbranched, alkoxy (preferably $C_1$-$C_4$ or $C_1$-$C_2$ alkoxy), where one or more substituent may be OH or a ketone.

In particular, non-limiting embodiments, $R_2$ is methyl, as in the native cocaine molecule.

In particular, non-limiting embodiments, $R_1$ is methoxy (as in the native cocaine molecule).

In other particular, non-limiting embodiments, $R_1$ is selected from the group consisting of methoxy, an activated N-hydroxysuccinimide ester, or another activated ester, for example an activated $C_1$-$C_6$ ester.

In other particular, non-limiting embodiments, $R_2$ is selected from the group consisting of methyl or (C=O) $C_2H_2COOH$ (succinic acid joined to the N via an amide bond).

In other particular, non-limiting embodiments, $R_2$ is methyl and $R_1$ is selected from the group consisting of methoxy, an activated N-hydroxysuccinimide ester, or another activated ester, for example an activated $C_1$-$C_6$ ester.

In alternative non-limiting embodiments, the pre-hapten is represented by Formula III:

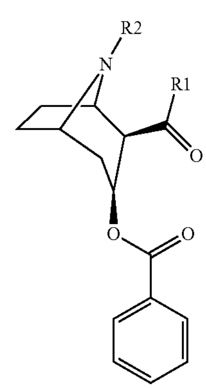

where $R_2$ is $CH_3$ (as in cocaine) and $R_1$ is selected from the group consisting of —O-tether-protein, N-tether-protein and N-protein (without tether) or, alternatively, $R_1$ is O—$CH_3$ (as in cocaine) and $R_2$ is selected from the group consisting of tether-protein and -protein (without tether).

Based on the foregoing a skilled artisan would be able to prepare analogous "pre-hapten" forms of other drugs, such as but not limited to nicotine, phencyclidine or heroin, suitable for reaction with Self protein.

Suitable tethers include, but are not limited to, aminocaproic acid, aminovaleric acid, aminobutyric acid, and aminoacetic acid.

5.2 Preparation of Drug/Self Protein Conjugates

Drug/Self protein conjugate may be prepared by any method known in the art that would be suitable for joining a drug pre-hapten, as set forth above, to a Self carrier protein. For example, methods previously used in the art to join cocaine to an immunogenic (non-Self) protein may be used to produce the cocaine/Self protein conjugates of the invention. See, for example, Carrera et al., 1995, Nature 378:727-730; Sakurai et al., 1996, Tetrahedron Lett. 5479-5482; Hrafnkelsdottir et al., 2005, Biol. Pharm. Bull. 28(6): 1038-1042; Fox et al., 1996, Nature Medicine 2(10):1129-1132; Haney and Kosten, 2004, Expert Rev. Vaccines 3:11-18 and Deng et al., Proc. Natl. Acad. Sci. U.S.A. 99: 3412-3416. Reactions to form benzoyl ecgonine and its acylation product are shown in FIG. 1A. Reaction of benzoyl ecgonine N-hydroxysuccinimide ester of cocaine to form a cocaine/protein conjugate is shown in FIG. 1B. Non-limiting examples of various cocaine/protein conjugates are shown in FIG. 2.

In preferred non-limiting embodiments, the linkage to carrier protein is via an ε-amino group of a lysine residue of the protein; preferably conjugation to more than one lysine is achieved and conjugation is to surface lysine residues to avoid disruption to the tertiary structure of the protein.

Non-limiting examples of synthetic schemes are depicted in FIGS. 3A-C.

For example, and not by way of limitation, 10 mg of benzoyl ecgonine in 5 ml tetrahydrofuran ("THF") may be added to 1.1 equivalent N-hydroxysuccinimide (NHS) and 1.1 equivalent of Ethyl 3-(3-dimethylaminopropyl)-3-ethylcarbodiimide hydrochloride (EDC). The reaction mixture may be stirred at room temperature for about 30 min. The solvent may then be removed under reduced pressure and the resultant cocaine activated ester, cocaine-NHS (a cocaine pre-hapten), may be dissolved in 0.2 ml of DMF and mixed with 5 mg of carrier Self protein in 1 ml PBS. The mixture may then be stirred for about 3 hour at about 4 C.° to provide cocaine/Self protein conjugate. The foregoing amounts may be varied depending on the desired yield of conjugate. In preferred non-limiting embodiments, the carrier Self protein may be HSA or MSA or TSA.

In preferred non-limiting embodiments of the invention, more than one cocaine hapten is conjugated to Self protein, for example, but not by way of limitation, between about 2 and 30 or between about 5 and 25 or between about 10 and 25 cocaine haptens may be conjugated per Self protein, or between about 10 and 100 percent or between about 20 and 80 percent or between about 50 and 80 percent of surface lysines of the Self protein may be conjugated to cocaine hapten. The degree of conjugation may be increased by increasing the concentration of cocaine pre-hapten relative to Self protein and/or increasing the reaction time.

Optionally, and not by way of limitation, the ability of a synthetic cocaine/Self protein conjugate to generate anti-cocaine antibodies may be assessed by determining whether the conjugate binds to an anti-cocaine antibody where said binding is competitively inhibited by the presence of free cocaine, for example an antibody of a human cocaine user or an experimental animal exposed to cocaine, where binding of said antibody to the conjugate is consistent with (bears positive correlation to) the ability of the conjugate to generate anti-cocaine antibodies when used as an immunogen. Monoclonal versions of such antibodies may be particularly effective for this purpose (see below).

Conjugates of other drugs to Self protein may be prepared using methods known in the art. For example, but not by way of limitation, trans-3'-aminomethylnicotine may be linked to Self protein through a succinic acid linker (see Pentel et al., 2000, Pharmacol. Biochem. Behav. 65: 191-198 and Fattom et al., 1993, Infect. Immun. 61: 1023-1032), or by other methods, for example methods that link nicotine to an ε-amino group of Self protein.

5.3 Pharmaceutical Compositions

The present invention provides for a pharmaceutical composition (which may be alternatively referred to as a "vaccine") comprising a drug/Self protein conjugate (e.g. cocaine/Self protein conjugate), in an amount effective at inducing an immune response to the drug in an immunocompetent subject, together with a suitable pharmaceutical carrier. Suitable pharmaceutical carriers include but are not limited to, water, saline, (e.g., saline that is isotonic to serum), Phosphate-buffered saline (PBS), Tris-buffered saline (TBS, HEPES-buffered saline (HBS) etc. In non-limiting embodiments, a sustained release formulation may be used.

An effective amount is the amount of drug/Self protein conjugate (e.g. cocaine/Self protein conjugate) which produces an antibody response against the drug (e.g. cocaine) when administered to an immunocompetent subject, as determined by methods known in the art. For example, in particular, non-limiting embodiments, inoculation with the effective amount, within about four weeks, increases antibody titers in an immunocompetent subject, who (i) either has or has not been previously exposed to cocaine (or the drug) but (ii) has not received the cocaine/Self protein conjugate previously, to a titer of at least about 1000 (referring to a 1:1000 dilution of immune serum which gives a signal to noise ratio of at least about 50:1) or at least about 10,000 (referring to a 1:10,000 dilution of immune serum which gives a signal to noise ratio of at least about 50:1), as measured by standard techniques, for example by enzyme linked immunosorbent assay ("ELISA")).

A pharmaceutical composition according to the invention may further comprise one or more adjuvant, for example, but not by way of limitation, aluminum phosphate, aluminum hydroxide, calcium phosphate, an oil emulsion such as MF-59, Montanide ISA 720, Adjuvant 65 (Maurice Hilleman's formulation), or Lipovant, a muramyl dipeptide derivative e.g. threonyl muramyl dipeptide, monophosphoryl lipid A, an ISCOM such as QS21 or Quil A, or MF-59, CpG, Advax, for nasal inoculation RhinoVax or other glyceride adjuvant or nanoemulsion adjuvant, or virosomes, or any adjuvant known in the art.

In particular, non-limiting embodiments, said pharmaceutical composition comprises between about 2 and 1000 micrograms, or between about 50 and 500 micrograms, or between about 10 and 200 micrograms; or between about 20 and 80 micrograms, or about 100 micrograms; of drug/Self protein conjugate (e.g. cocaine/Self protein conjugate).

In a particular non-limiting embodiment, drug/Self protein conjugate (e.g. cocaine/Self protein conjugate) may be comprised in a liposome.

A pharmaceutical composition according to the invention may be in liquid or solid form, may be in powder form or aerosol form, and may be comprised in a sustained release formulation.

In liquid form, a pharmaceutical composition may comprise a suitable liquid for example but not limited to sterile water or physiologic saline.

5.4 Methods of Use

The present invention provides for a method of treating a subject in need of such treatment to diminish the subject's response to and/or use of a drug such as cocaine, comprising administering, to the subject, a pharmaceutical composition (vaccine) comprising an immunogenic amount of a drug (e.g., cocaine)/Self protein conjugate, as described above.

A subject in need of such treatment may be a subject who is physically or behaviorally dependent on the drug (e.g., cocaine) and/or circumstances are such that it is desirable to reduce the subject's response to and/or use of the drug. "Treatment" may comprise a decrease in the subject's response to the drug and/or a decrease in frequency of the subject's use of the drug and/or a decrease, which may be subjective and/or objective, in the dependency of the subject on drug use.

In various non-limiting embodiments, the pharmaceutical composition may be administered intramuscularly, subcutaneously, intradermally, nasally, orally, by rectal or vaginal suppository, intravenously, or by any other method known in the art.

In particular, non-limiting embodiments, the present invention provides for a method of treating a subject in need of such treatment to diminish the subject's response to and/or use of a drug such as cocaine, comprising (i) administering, as a primary inoculation, a pharmaceutical composition (vaccine) comprising a first immunogenic amount of a drug (e.g., cocaine)/Self protein conjugate, as described above and, after a time interval, (ii) administering, as a booster inoculation, a pharmaceutical composition (vaccine) comprising a second immunogenic amount of a drug (e.g., cocaine), where the amount of conjugate in the primary inoculation and the booster inoculation may be the same or different. In further related embodiments, more than one booster inoculation, for example, two, three, or four boosters, or a booster every several months or every several years, may be administered.

The time interval between primary inoculation and booster inoculation may be, for example and not by way of limitation, between 5 days and 30 days, or between 5 days and 60 days, or between 5 days and 90 days, or between 5 days and 120 days, or between 5 days and 150 days, or between 5 days and 180 days, or between 5 days and one year, or between 5 days and 2 years, or between 5 days and 5 years.

Where a sustained release formulation is provided, the time interval may be greater.

In certain embodiments a booster inoculation may not be required. Further, once a subject achieves protective immunity, future use of drug (e.g., cocaine) may result in in vivo conjugation of drug to mimic the immunogen and act as an endogenously generated booster.

Specific non-limiting examples of immunization schedules are as follows: (i) primary inoculation at day 0, first booster at day 10-30; (ii) primary inoculation at day 0, first booster at day 10-30, second booster at day 30-60; (iii) primary inoculation at day 0, first booster at day 10-30, second booster between 10-30 days after first booster; (iv) primary inoculation at day 0, first booster at day 10-30, second booster between 10-20 days after first booster, third booster between 10-30 days after second booster; (v) primary inoculation at day 0, first booster at day 10-30, second booster between 10-30 days after first booster, third booster between 10-30 days after second booster, fourth booster between 30-60 days after third booster; (vi) primary inoculation at day 0, first booster at least 5 days after primary inoculation; or (vii) any of the above followed by one or more boosters at three month, six month, one year, two year, or five year interval(s).

In particular, non-limiting embodiments, one or more booster inoculation is administered to maintain an anti-cocaine antibody levels of at least or higher than 50 ug/ml of blood plasma.

Vaccinated patients will develop antibodies against drugs (e.g., cocaine). Such vaccinated patients may serve as donors for B-cells which can be used to generate human hybridomas producing monoclonal antibodies against drugs (e.g., cocaine). Such antibodies can be potentially beneficial therapeutically, for example for treating an overdose. Accordingly, the present invention, in particular non-limiting embodiments, provides for a hybridoma and a monoclonal antibody produced thereby prepared by immunizing a human subject with an immunogenic amount of a conjugate of the invention, wherein the monoclonal antibody specifically binds to cocaine; the invention also provides for a pharmaceutical composition comprising such monoclonal antibody.

6. EXAMPLE 1

To better understand the relationship between the human immune system and cocaine, lymphocytes were harvested from persons who had a history of cocaine use. These lymphocytes were then fused with the immortal human MFP-2 cell line to produce hybridomas. Fully human antibodies produced by the resulting hybridomas were then screened by ELISA, using cocaine coupled to BSA (bovine serum albumin) using a 10-atom linker via the nitrogen of tropane group of cocaine as target antigen, to identify hybridomas that produce anti-cocaine antibodies. Characteristics of anti-cocaine antibody-producing hybridomas identified are shown in FIG. 4. These four hybridoma lines all produced IgM isotype antibodies, consistent with a primary immune response. Of note, protective immunity against an antigen is typically associated with a secondary immune response characterized by antibodies of the IgG isotype. This supports the clinical observation that levels of naturally occurring anti-cocaine antibodies do not confer protection against the effects or usage of cocaine.

To study the binding specificities of these antibodies, two different forms of cocaine conjugates were used. The first, designated "CM", linked cocaine to either bovine serum albumin ("BSA") or ovalbumin ("OVA") as a benzoyl ecgonine ester (FIG. 5B). The second, designated "N", linked cocaine to BSA or OVA via the nitrogen of the tropane group (FIG. 5C).

FIG. 5A shows the results of ELISA screening of human hybridomas, for monoclonal antibodies to cocaine conjugates BSA-N, BSA-CM, OVA-CM or OVA-N. The human antibodies were used at a dilution of 1:50. A commercial anti-cocaine murine monoclonal antibody was tested at a dilution of 1:10,000. These results indicate that all three human monoclonal antibodies (1D7, 1D8D6, and F2D4) bound to both BSA-N and OVA-N; only 1D7 bound to BSA-CM, and 1D7 and 1D8D6 showed substantial binding to OVA-CM. For all three human monoclonal antibodies, greater binding to "N" rather than "CM" linked conjugates was observed.

In a second series of experiments, plates were coated with the BSA-N cocaine conjugate, and then the ability of antibodies to bind to the plate was tested in the presence of cocaine. If an antibody were substantially recognizing cocaine in the conjugate, then increasing concentrations of cocaine should progressively decrease the amount of antibody bound to the plate. The results are shown in FIG. 6A-C. Binding of murine anti-cocaine antibody, at 1:20,000 dilution, was effectively blocked by increasing concentrations of cocaine. Binding of the fully human monoclonal antibodies was also competitively blocked by cocaine, demonstrating their specificity toward the small molecule (FIGS. 6A and B). As a control, FIG. 6C shows that free cocaine conjugate BSA-N was able to effectively compete with the same bound capture antigen for binding with antibodies.

Next, the ability of commercial mouse monoclonal anti-cocaine antibody to bind to cocaine naturally (spontaneously) incorporated into to human and rat serum proteins was tested. FIG. 7A-C shows the incorporation of anti-benzoyl ecgonine immunoreactivity into proteins. SDS/PAGE chromatography and Western blotting with mouse MAB 46H1 of samples are shown: (A) HSA (control, lane 1); HSA incubated with cocaine for 3 days and immunoprecipitated with MAB 46H1 (HAS+COC, lane 2); and benzoyl ecgonine-linked HSA (BE-HSA, lane 3); (B) plasma from rats exposed to cocaine twice daily for 7 days (lanes 1-6) and plasma from unexposed control (lane 7, C) immunoprecipitated with MAB 46H1; and (C) plasma from human cocaine users (lanes 1-6) and an unexposed control subject (lane 7 C) immunoprecipitated with MAB 46H1.

FIG. 8A-D shows the binding of various dilutions of monoclonal antibodies (A) fully human 1D8D6; (B) fully human 1D7; (C) fully human F2D4 or (D) murine anti-cocaine monoclonal antibody to either Coc-HSA 1, Coc-HSA-2, Coc-HSA-3, Coc-HSA 4, or Coc-N-BSA.

7. EXAMPLE 2

Experiments were performed to test whether a synthetic cocaine-plasma protein conjugate that resembled conjugate formed in vivo would be able to induce an anti-cocaine immune response. As studies were performed in mice, the murine Self protein murine serum albumin ("MSA") was selected as a carrier. A cocaine conjugate was prepared by first generating, as a cocaine pre-hapten, benzoyl ecgonine N-hydroxysuccinimide ester, and then reacting the pre-hapten with MSA. This was then used to immunize mice using the following protocol.

1.5 mg of cocaine-MSA was suspended in 1 ml of PBS. 0.5 ml of Complete Freund's Adjuvant (CFA) was added to this solution and vortexed for 45 minutes. The final suspension containing 1.0 mg/ml of cocaine-MSA and 30% CFA was loaded to tuberculin 1 cc syringe and 50 ul were administered into left flank of BALB/C mice (~6 weeks old females). Two mice received inoculations of this immunogen on days 0, 5, 20, 32 and 40 (mice ##1 and 2), two mice received inoculations on days 0, 8, 20 and 28 (mice ##3 and 4) and 1 mouse received inoculations on days 0 and 10 (mouse #5). The first inoculations in mice ##1-4 were done at 50 ug/mouse in CFA and all the following at 50 ug/mouse in Incomplete Freund's Adjuvant (IFA). The first inoculation in mouse #5 was done with $10^6$ syngeneic dendritic cells pulsed with cocaine-MSA and the following with 50 ug/mouse of conjugate in IFA. On days 21, 30 and 50 (mice #1 and 2), days 7, 15 and 38 (mice #3 and 4) and day 21 (mouse #5) the sera of these mice was tested for the presence of anti-cocaine antibodies, using a standard ELISA method and either MSA or cocaine-MSA conjugate as capture antigen. The results are shown in FIGURES. All mice demonstrated anti-conjugate antibody titers ranging from 100,000 to 1,000,000. The fact that there was no reactivity between any of the three antisera with MSA indicates that the mice had developed a strong immune response specifically directed against cocaine. Using immune sera the estimate of mouse polyclonal antibodies against MSA-o-tet-Coc was made. Competitive ELISA was used for this purpose and both MSA-0-tet-Coc and free cocaine were used as competitors. The results of these experiments are presented on FIGS. 10 and 11.

FIG. 10 shows the log-logit regression plots for MSA-0-tet-Coc completion assay. The Ka of antibodies reactive with MSA-0-tet-Coc is approximately $10^{-9}$M, while the Ka for antibodies reactive with free cocaine is approximately $10^{-6}$M (FIG. 11, log-logit regression analysis.)

8. EXAMPLE 3

The immunoreactivity of mouse monoclonal antibody against MSA-0-tet-Coc and total human serum protein modified with cocaine using 0-tether was tested. SDS PAGE and Western blotting showed that benzoyl ecgonine specific mouse monoclonal antibody strongly reacts with MSA-0-tet-Coc on a blot (FIG. 12, lane 3) as well as with a number of human serum proteins modified with cocaine hapten (FIG. 12, lanes 1 and 2). There was no immunoreactivity whatsoever with MSA or non-modified human serum proteins. Among human serum proteins which were able to conjugate with cocaine under controlled synthesis and through a 0-tether HSA, light and heavy chains of immunoglobulins and α2-macroglobulin were clearly identifiable.

9. EXAMPLE 4

9.1 Materials and Methods

Synthesis of Cocaine Immunoconjugate Vaccine.

The MSA-coc and mIg-coc immunoconjugates were successfully synthesized through a one-step conjugation synthesis (FIG. 3A). ELISA and Western blotting analyses were performed using anti-coc antibodies in order to provide proof of cocaine coupling to MSA or mIgG (FIG. 13).

Active Immunization of Mice.

After injecting mice with the MSA-coc or mIg-coc conjugates, the generation of anti-coc antibodies in sera was tested by ELISA. In these assays, use of ovalbumin-cocaine (OVA-coc) allowed for direct analysis of solely the titers of anti-coc antibodies generated, as ovalbumin is evolutionarily distant from MSA or mIgG and contains no common epitopes. The assays indicated the robust generation of antibodies against cocaine in mouse sera upon injection of MSA-coc or mIg-coc, verifying the efficacy of the novel vaccines (FIGS. 14A-B). ELISA also provided a characteristic curve for anti-coc immune titers. Moreover, the dose, frequency, and adjuvant were varied through multiple trials in order to optimize the titers of antibodies generated against cocaine, and titer levels were continually monitored by periodic ELISA testing.

9.2 Results

Physiological Effects.

In order to determine the therapeutic and physiological effects of the conjugate vaccine in vivo, a number of cocaine challenge experiments were conducted on immune (MSA-coc vaccinated) and non-immune mice. Non-immune mice injected with PBS served as the control group, and the mice were either immunized with MSA-coc or injected with PBS at the same frequency (see Methods). MSA-coc was utilized because the conjugate more efficiently generated anti-coc antibodies. The mice were then challenged with cocaine at three different doses: the effective dose (ED100), median lethal dose (LD50), and absolute lethal dose (LD100). The data presented in Table 1 demonstrate the efficacy of the MSA-coc vaccine. While the non-immune control group was affected according to the dose in expected ratios, the immune mice displayed significantly disparate behavior. Absolutely none of the immune mice exhibited any stimulatory effects at ED100, while 100% of the control group was affected at the same dose. More dramatically, none of the immunized mice succumbed to cocaine overdose at either LD50 or LD100, compared to 4 and 9 deaths at each respective dose for the control group. These studies provide substantive evidence that the MSA-coc conjugate vaccine is an effective therapy against cocaine dependency and prevents cocaine from gaining access into the CNS.

competitive antigen for both assays. When MSA-coc and TA-CD were analyzed as competitors, the characteristic curve was generated. However, contrasting results were obtained in assays in which MSA-coc and TA-CD were pre-incubated with CocE (FIG. 17).

While there were little to no effects on antibody binding to MSA-coc pre-treated with CocE, antibody binding to TA-CD under the same conditions was utterly nullified. These results confirm the hypothesis that vaccines developed according to prior art, using long tethers for conjugation, make the cocaine molecules substantially vulnerable to esterase hydrolysis, resulting in the failure to generate an adequate immune response in vivo.

9.3 Discussion

Structural Design.

Prior approaches, for example Kosten et al. (2002, Vaccine 20:1196-2004), present a number of disadvantages, primarily in that the anti-coc immune response is substantially diluted by irrelevant antibodies. On a structural basis, nearly 80% of the antibodies generated can be thus categorized. This is believed to result from the use of a foreign protein and tether molecule (DCC-derivatized 4-atom linker) which leads to the formation of a number of neoepitopes. Consequently, antibodies must be developed against: a) the carrier protein, b) linker molecule, c) cocaine

TABLE 1

Effects of cocaine challenge at effective dose ($ED_{100}$), median lethal dose ($LD_{50}$), and absolute lethal dose ($LD_{100}$) on non-immune control mice and experimental mice immunized with MSA-coc. Results shown are the averages of three independent experiments.

| Cocaine challenge | Control group, 10 mice (non-immune) | | | | Experimental group, 10 mice (immunized with MSA-coc) | | | |
|---|---|---|---|---|---|---|---|---|
| (mg/kg) | survival | fatality | hyper | seizures | survival | fatality | hyper | seizures |
| 0 | 10 | 0 | 0 | 0 | 10 | 0 | 0 | 0 |
| 50 ($ED_{100}$) | 10 | 0 | 10 | 1 | 10 | 0 | 0 | 0 |
| 100 ($LD_{50}$) | 6 | 4 | 10 | 7 | 10 | 0 | 2 | 0 |
| 180 ($LD_{100}$) | 1 | 9 | 10 | 10 | 10 | 0 | 7 | 2 |

Cocaine Degradation Rates in Immune and Non-Immune Sera.

Initial experiments revealed that the dilution of mouse serum in PBS results in a decreased rate of cocaine degradation in vivo (FIG. 15).

The kinetics of cocaine degradation in immune and non-immune mouse sera was then studied by mass spectroscopy to discern the pharmacological effects of anti-coc antibodies. Although degradation rates were nearly uniform in all non-immune mice (FIG. 16A), significant differences existed in the rates in immune mice, depending on the titer of anti-coc antibodies in the plasma (FIG. 16B). As the titers increased, the degradation rates conversely decreased, contrary to original expectations. These results indicate that antibodies shield cocaine from degradation upon binding, prolonging the circulation of cocaine in serum.

Effect of Esterases on Antibody Binding to Immunoconjugates.

Competition ELISA was conducted on MSA-coc and Cholera toxin B-chain coupled to cocaine through 4-atom tether (TA-CD vaccine, Kosten et. al (2002, Vaccine 20:1196-2004))] to examine how the presence of esterases in serum would affect the vaccine structure and binding of anti-coc antibodies to the conjugates. OVA-coc served as the derivative, d) overlap between the linker and cocaine, and e) overlap between the linker and the carrier (FIG. 19A). As antibodies are only desired against the cocaine derivative, the vast majority of the immune response would be entirely superfluous for cocaine immunotherapy.

In contrast, the present invention provides a novel conjugate vaccine using a self-protein approach where there is either no tether or the tether is essentially non-immunogenic. By using a self-protein, for example, MSA or mIgG, in the murine model, the generation of anti-carrier antibodies is almost eliminated. Furthermore, the lack of a tether through direct conjugation of lysine ε-amino groups to intact cocaine molecules minimized the potential for neoepitopes formed by hapten-linker or carrier-linker overlap sites, or the linker itself. Thus, the preponderance of antibodies generated against the inventive conjugate vaccine would be directed towards cocaine itself (see FIG. 19B). Both ELISA and Western blotting demonstrated the presence of cocaine on the carrier protein, indicating the success of the conjugate synthesis process. The demonstration of robust anti-coc antibody titers in immunized mouse sera was significant in that it confirmed the generation of the desired immune response by MSA-coc and mIg-coc. ELISA showed that immune response to any foreign neoepitopes was negligible for the conjugates, substantiating the vaccine's efficiency in generating anti-coc antibodies in vivo.

Effect of Immunization on Physiological Response to Cocaine Challenge.

As Table 1 indicates, the immunization of mice with the MSA-coc vaccine has a dramatic impact on the physiological response to cocaine injection. None of the mice immunized with MSA-coc expired upon the injection of LD100 concentration of cocaine, compared to a 90% fatality rate in the control group. Even at this dose, there was little discernable indication of stimulation in locomotor activity or stereotyped behavior. The results therefore show that MSA-coc indeed holds substantial potential for cocaine immunopharmacotherapy.

Antibody-Induced Protection of Cocaine from Degradation.

As shown in FIG. 16A-B, increasing anti-coc antibody titers in serum decreases the rate of cocaine degradation, signifying that antibody binding blocks the ester bonds of cocaine from esterase hydrolysis. Such shielding would be expected to prolong the circulation of the bound cocaine without access across the blood-brain barrier, providing valuable ramifications for immunotherapy. For example, because the interval for antibody response is protracted, a "snowball" effect would result: throughout the circulation of the antibody-bound cocaine, further anti-coc antibodies would be generated against the bound hapten, acting as a perpetual anti-idiotypic vaccine, which has established anti-cocaine effects in vivo (Schabacker et al., 2000, Immunol. 100:48-56). This effect would accumulate with the continuous production of additional antibodies, resulting in a more robust and long-lasting immune response.

Vulnerability of Tethered Cocaine to Esterase Hydrolysis.

Upon clinical trials of TA-CD, it was found that nearly 30% of all vaccinated patients failed to produce sufficient antibody titers after multiple inoculations (Sufuoglu et al., 2006, Expert Opin. Emerg. Dr. 11:91-98). This was a substantial detriment to the efficacy of the vaccine as a form of pharmacotherapy, and severely limited its clinical utility; yet no causal factor could be determined for this lack of efficacy (Orson et al., 2008, Ann. N.Y. Acad. Sci. 1141:257-269). It was conjectured from the TA-CD structure that the use of a tether molecule significantly increased the vulnerability of the cocaine to esterase hydrolysis in vivo. This is because the tether binds the cocaine to a large carrier and considerably reduces its diffusion capacity, while forming protruding, salient targets for enzymatic degradation. Thus, if the bound cocaine molecules are rapidly hydrolyzed upon injection, an immune response cannot generated against cocaine.

It is important to note that unlike commercial test mice, humans possess a tremendous spectrum of phenotypic variation. In other words, certain individuals possess atypically effective BChE and other nonspecific esterases, corresponding to the percentage of vaccinated patients who failed to generate an immune response (Kalow et al., 1957, Can J. Biochem. Physiol. 35:339-346). Consequently, it was hypothesized that patients who possessed efficient serum esterases were resistant to the vaccine developed by prior art.

These results demonstrate that the use of a tether significantly increases vulnerability to esterase hydrolysis. The addition of CocE through competition ELISA rendered TA-CD entirely non-immunogenic for anti-coc antibodies. These findings indicate that cocaine is swiftly degraded by esterases in TA-CD, resulting in a deficient or nonexistent immune response and providing a valid explanation for its lack of therapeutic efficacy. On the other hand, the absence of any noticeable effects of CocE on antibody binding to MSA-coc confirms that the cocaine is protected from degradation by the MSA carrier. This presents another advantage for our vaccine design: the shielding of cocaine haptens by surface steric effects through the removal of a tether.

Various publications are cited herein, the contents of which are hereby incorporated by reference in their entireties.

We claim:

1. A cocaine pre-hapten having Formula II:

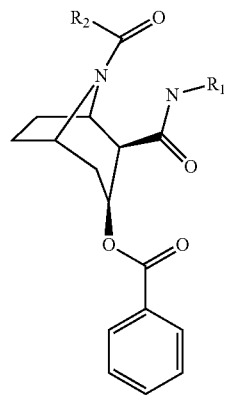

wherein $R_1$ and $R_2$ are the same or different, and $R_1$ and $R_2$ are independently:
  unsubstituted or substituted, branched or unbranched, alkyl; or
  unsubstituted or substituted, branched or unbranched, alkoxy.

2. A conjugate formed between a cocaine pre-hapten of claim 1, and a serum protein selected from the group consisting of human serum albumin, human alpha 2 macroglobulin, and human immunoglobulin.

3. The conjugate of claim 2, wherein the serum protein is a human immunoglobulin.

4. A composition comprising the conjugate of claim 2, in a suitable carrier.

5. The cocaine pre-hapten of claim 1, wherein one or both of $R_1$ and $R_2$ are:
  unsubstituted or substituted, branched or unbranched, $C_1$-$C_4$ alkyl; or
  unsubstituted or substituted, branched or unbranched, $C_1$-$C_4$ alkoxy.

6. The cocaine pre-hapten of claim 1, wherein one or both of $R_1$ and $R_2$ are:
  unsubstituted or substituted, branched or unbranched, $C_1$-$C_2$ alkyl; or
  unsubstituted or substituted, branched or unbranched, $C_1$-$C_2$ alkoxy.

7. The cocaine pre-hapten of claim 1, wherein one or both of $R_1$ and $R_2$ comprise one or more substituents selected from a hydroxyl (OH) and a ketone (=O).

* * * * *